(12) United States Patent
Dowling

(10) Patent No.: US 12,201,742 B2
(45) Date of Patent: Jan. 21, 2025

(54) HYDROPHOBICALLY-MODIFIED BIOPOLYMER MATERIALS

(71) Applicant: MEDCURA, INC., Riverdale, MD (US)

(72) Inventor: Matthew Dowling, Riverdale, MD (US)

(73) Assignee: MEDCURA, INC., Riverdale, MD (US)

( * ) Notice: Subject to any disclaimer, the term of this patent is extended or adjusted under 35 U.S.C. 154(b) by 180 days.

(21) Appl. No.: 17/765,953

(22) PCT Filed: Oct. 5, 2020

(86) PCT No.: PCT/US2020/054268
§ 371 (c)(1),
(2) Date: Apr. 1, 2022

(87) PCT Pub. No.: WO2021/067938
PCT Pub. Date: Apr. 8, 2021

(65) Prior Publication Data
US 2022/0347341 A1    Nov. 3, 2022

Related U.S. Application Data

(60) Provisional application No. 62/910,080, filed on Oct. 3, 2019.

(51) Int. Cl.
*A61L 24/08* (2006.01)
*A61L 24/00* (2006.01)

(52) U.S. Cl.
CPC ........... *A61L 24/08* (2013.01); *A61L 24/0031* (2013.01); *A61L 2400/04* (2013.01)

(58) Field of Classification Search
None
See application file for complete search history.

(56) References Cited

U.S. PATENT DOCUMENTS

| | | | |
|---|---|---|---|
| 8,668,899 B2 | 3/2014 | Dowling et al. | |
| 8,932,560 B2 | 1/2015 | Dowling et al. | |
| 9,066,885 B2 | 6/2015 | Raghavan et al. | |
| 9,616,088 B2 | 4/2017 | Diehn et al. | |
| 10,179,145 B2 | 1/2019 | Dowling et al. | |
| 10,493,094 B2 | 12/2019 | Diehn et al. | |
| 11,274,194 B2 | 3/2022 | Dowling | |
| 11,298,517 B2 | 4/2022 | Dowling et al. | |
| 11,787,922 B2 | 10/2023 | Dowling | |
| 2010/0135915 A1 | 6/2010 | Greener | |
| 2019/0083676 A1 | 3/2019 | Zilberman et al. | |

FOREIGN PATENT DOCUMENTS

| | | |
|---|---|---|
| WO | 2008076407 A2 | 6/2008 |
| WO | 2013043687 A2 | 3/2013 |
| WO | 2018184021 A1 | 10/2018 |
| WO | 2020181015 A1 | 9/2020 |

OTHER PUBLICATIONS

International Search Report and Written Opinion of corresponding International Application No. PCT/US20/54268 dated Jan. 12, 2021, 8 pages.
Nehache et al., "Anti-Bioadhesive Coating Based on Easy to Make Pseudozwitterionic RAFT Block Copolymers for Blood-Contacting Applications," Macromol Biosci. 2016, pp. 57-62.
Dowling, et al., "Hydrophobically-modified chitosan foam: description and hemostatic efficacy", J Surg Res. Jan. 2015; 193(1):316-23. doi: 10.1016/j.jss.2014.06.019. Epub Jun. 14, 2014.
Logun, et al., "Expanding Hydrophobically Modified Chitosan Foam for Internal Surgical Hemostasis: Safety Evaluation in a Murine Model", J Surg Res. Jul. 2019;239:269-277. doi: 10.1016/j.jss.2019.01.060. Epub Mar. 16, 2019.
Dowling, et al., "Sprayable Foams Based on an Amphiphilic Biopolymer for Control of Hemorrhage Without Compression", ACS Biomater Sci Eng. Jun. 8, 2015;1(6):440-447. doi: 10.1021/acsbiomaterials.5b00067. Epub May 2, 20159.

*Primary Examiner* — Shirley V Gembeh
(74) *Attorney, Agent, or Firm* — Morgan, Lewis & Bockius LLP

(57) ABSTRACT

In various aspects and embodiments, the present invention provides hemostatic products and methods for treating wounds, including cavity wounds and non-compressible hemorrhage. In various embodiments, the invention employs hydrophobically-modified polymer foams, gels, or pastes.

15 Claims, 18 Drawing Sheets

Vivo Study: 'Mashed Potatoes' like hmC paste applied on wound of a pig

2wt% hm-chitosan and 3wt% polyethylene oxide foam

2wt% hm-chitosan and 5 wt% Pluronic 123 foam

FIGURE 12A
FIGURE 12B
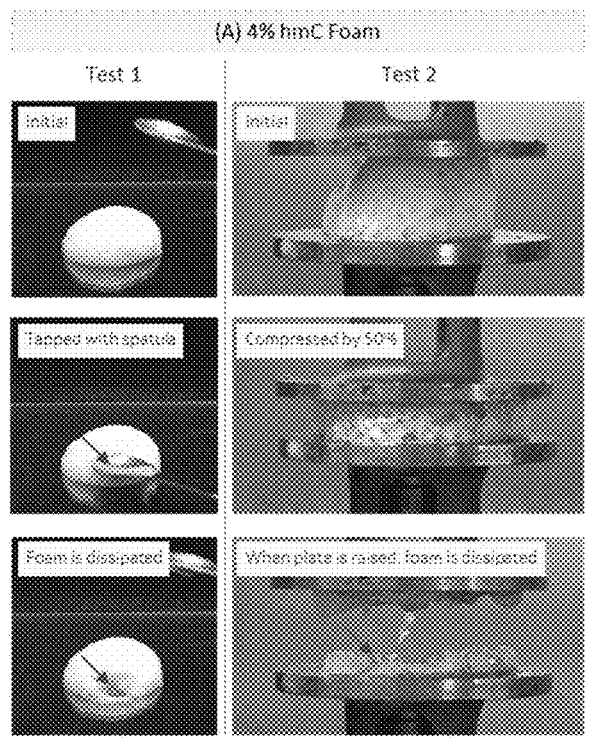
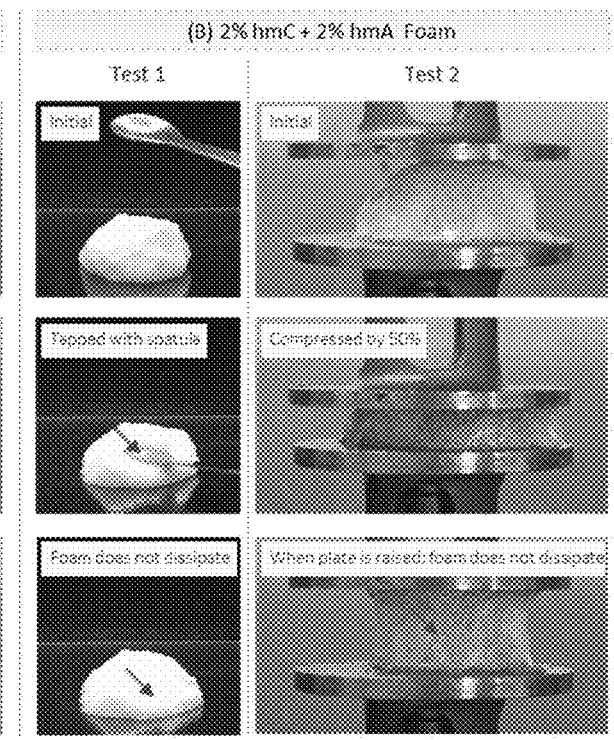

(A) hmC Foam

1. Foam applied to wound area

2. Foam allowed to sit

3. Blood leaks out through foam (B) hmC-hmA Foam

1. Foam applied to wound area

2. Foam allowed to sit

3. No blood leaks through foam

HYDROPHOBICALLY-MODIFIED BIOPOLYMER MATERIALS

CROSS-REFERENCE TO RELATED APPLICATIONS

This application is a National Stage Entry of PCT/US20/54268, filed on Oct. 5, 2020, which claims the benefit of U.S. Provisional Application No. 62/910,080, filed on Oct. 3, 2019, the entire contents of which are hereby incorporated in their entirety.

GOVERNMENT INTEREST

This invention was made with government support under Department of Defense grant W81XWH-18-1-0006. The government has certain rights in the invention.

FIELD

The present invention provides hemostatic products and methods for treating wounds.

BACKGROUND

Non-compressible hemorrhage is the leading cause of death due to traumatic bleeding, accounting for 90% of all hemorrhage-related deaths. Non-compressible hemorrhage refers to bleeding that is not accessible to direct pressure, and includes intracavitary bleeding from soft tissues within the abdomen, a common result of shrapnel injuries during military combat and car accidents within civilian settings.

Standard and advanced bandages which require compression to function properly are not applicable for non-compressible hemorrhage bleeds. Currently no effective solutions for non-compressible hemorrhage exist outside of surgical intervention. Because it may require several hours to transport an injured patient to the hospital, a clear need exists for products which can effectively stop non-compressible bleeding both initially on site and subsequently throughout the pre-hospital transfer period.

SUMMARY OF THE INVENTION

In various aspects and embodiments, the present invention provides hemostatic products and methods for treating wounds, including cavity wounds and non-compressible hemorrhage, and including surgical bleeds. In various embodiments, the invention employs hydrophobically-modified polymer foams, gels, or pastes.

In one aspect, the invention involves a hydrophobically-modified polymer foam as a hemostatic product. For example, the hemostatic product may comprise a device having at least two compartments each containing a releasable, flowable solution. The first compartment comprises a solution of an acidified hydrophobically-modified polymer that creates hemostasis in the presence of an injury. Such hemostasis is created when the hydrophobically-modified polymer gels in the presence of blood or creates an artificial clot or seal in the presence of blood. An exemplary hydrophobically-modified polymer is hydrophobically-modified chitosan. A second compartment comprises a solution of a bicarbonate or carbonate salt at an alkaline pH. Upon release of the contents through a mixing tip, the flowable products produce a stable foam (due to the production of $CO_2$) that will expand in a body cavity and produce an "artificial clot" or seal with blood cells, thereby resulting in hemostasis. The character and density of the hydrophobic grafts, and solution additives, ensure the production of a stable foam. In some embodiments, the hydrophobic modifications comprise or consist essentially of linear hydrocarbon groups having a variable size.

In some embodiments, the foaming action of the product enables expansion of the material inside a body cavity (e.g., "expansion phase"), and during this expansion, the foam adheres and attaches to tissue in the body cavity, resulting in a halting of the bleeding during the expansion phase. In accordance with embodiments of the invention, varying the hydrophobic chain length of the hydrophobically-modified polymer, with select hydrophobic grafting densities, allows for production of a stable foam that does not quickly dissipate. In some embodiments, the product comprises a double-barrel syringe comprising two compartments and a static mixing tip.

In some embodiments, the linear hydrocarbon groups (or "grafts") are from about C6 to about C18, or are from about C8 to about C18. In some embodiments, the hydrophobically-modified polymer has hydrocarbon grafts of at least two different sizes attached to the polymer backbone. For example, the hydrocarbon grafts can comprise at least a first hydrocarbon chain length of from C8 to C12, which is sufficient to provide hemostatic properties, and at least a second hydrocarbon chain length of C14 or greater, which provides improved blood gelling properties and foam integrity.

In some embodiments, the hydrophobically-modified polymer has hydrocarbon grafts of at least three different sizes attached to the polymer backbone. In some embodiments, the hydrophobic grafts comprise a combination of the following linear, saturated, hydrocarbon grafts: (a) grafts of C6 to C8 in length; (b) grafts of C10 to C14 in length; and (c) grafts of C16 to C18 in length. This combination of hydrocarbon grafts can provide strong blood gelling properties while also producing a stable foam. Further, the viscosity is amenable to dispensing through a double-barrel syringe.

In some embodiments, the modified polymer is amphiphilic. In some embodiments, the polymer is based on a polysaccharide backbone, such as chitosan, alginate, gelatin, cellulosic, pectin, gellan gum, xanthan gum, dextran, and hyaluronic acid, among others. In some embodiments, the polymer is a synthetic (i.e., non-natural) polymer, such as polyethylene glycol, poly-lactic acid, poly-glycolic acid, poly lactic co-glycolic acid, poly lactic co-glycolic acid, polymethylmethacrylate, poly &-caprolactone, polyurethane, silicone, among others. In some embodiments, the modified polymer is hydrophobically-modified chitosan. In some embodiments, the polymer is hydrophobically-modified alginate or hydrophobically-modified gelatin.

The first compartment of the container contains an acidic solution of the hydrophobically-modified polymer. In some embodiments, the principal solvent is water with an organic acid. In some embodiments, the organic acid is selected from one or more of acetic acid, lactic acid, ascorbic acid, and citric acid, and having a pH of from about 2 to about 4.5. For example, in the case of acetic acid and hm-chitosan, the acetic acid may be from 0.5M to 2M (e.g., about 1M). The second compartment of the container comprises a solution of a carbonate or bicarbonate salt, such as a bicarbonate salt (e.g., sodium bicarbonate). In some embodiments, the bicarbonate solution is from about 0.5 to about 2M (e.g., about 1M). The bicarbonate or carbonate solution may be at pH 8 to pH 14. In various embodiments, the first or second compartment further comprises one or more foam stabilizing additives. In some embodiments, the second compartment further comprises a polymer selected from gelatin, alginate, dextran, polyethylene oxide, hydroxyethylcellulose, and hydropropylcellulose. In some embodiments, the polymer added to the second compartment is anionic. In further embodiments, the polymer additive may also be hydrophobically modified. For example, the polymer added to the second compartment may be anionic (e.g., alginate or hm-alginate), and the hydrophobically-modified polymer in the first container may be cationic (e.g., chitosan). Upon releasing the flowable contents, the polymers will form a coacervate.

In another aspect, the invention provides a gel or paste based on the hydrophobically-modified polymer. In accordance with this aspect of the invention, hydrogel particles or granules, such as quaternized dimethylaminoethyl methacrylate (QDM) or dextran particles, are incorporated into the hydrophobically-modified polymer solution. The resulting material will have paste-like characteristics that is easy to handle and apply, e.g., to treat or manage surgical bleeding. Further the material will create flow-resistance against blood that would enter the polymer matrix upon application to a bleeding site. In these embodiments, the hemostatic product is useful for treating minor soft tissue bleeds.

A product of the present disclosure may be used in methods related to treating a wound, including but not limited to non-compressible hemorrhage, cavity bleeds including soft tissue bleeds and internal bleeding during surgery. In various embodiments, the wound is treated by releasing the contents of the product onto the site of bleeding. For example, the contents of the container may be released into one or more body cavities to halt a cavity bleed or non-compressible hemorrhage. The contents of the container may also be released into one or more body cavities during surgery. In some embodiments, the flowable product expands by foaming action in the cavity. In some embodiments, the wound has high exudate or blood flow. In some embodiments, the gel or paste employing hydrophobically-modified polymer is applied to a bleeding wound, such as a soft tissue bleed during surgery.

Other aspects and embodiments of the invention will be apparent from the following detailed disclosure.

BRIEF DESCRIPTION OF THE FIGURES

FIG. 10A shows solutions of 2% chitosan and 2% alginate forming a coacervate. FIG. 10B shows similar coacervation with mixtures of hydrophobically-modified chitosan (hmC) and hydrophobically-modified alginate (hmA).

FIG. 11A shows an hmC foam, where one barrel of the DBS has hmC dissolved in acetic acid ($CH_3COOH$) while the other barrel has a sodium bicarbonate ($NaHCO_3$) solution. FIG. 11B shows an hmC-hmA foam, where the second barrel of the DBS contains hmA dissolved in $NaHCO_3$. In this case, the bubbles in the foam are stabilized by both hmC and hmA chains, which are collectively expected to form a coacervate.

FIGS. 12A-B depicts a visual comparison of an hmC foam and an hmC-hmA foam, where both foams have a total polymer concentration of 4 wt %. The first test involves tapping the foam with a spatula, and the second test involves compressing the foam between parallel plates to half of its initial height for 1 minute, and then the top plate being raised back up.

In FIGS. 14A and 14B, data are compared for a 4% hmC foam and a 2% hmC+2% hmA foam (same total polymer content). The data plotted are for the elastic modulus G' (filled circles) and the viscous modulus G" (unfilled triangles) as functions of the frequency (FIG. 14A) and the stress-amplitude (FIG. 14B) at a constant frequency of 10 rad/s. In FIG. 14C, G' values for hmC and hmC-hmA foams are plotted against the total polymer concentration. In FIG. 14D, the same G' data are plotted against the average bubble diameter in the foams.

FIG. 15A shows a tube filled with blood and foam with only hmC, and FIG. 15B shows a tube filled with blood and foam containing hmC and hmA.

DETAILED DESCRIPTION OF THE INVENTION

Figure 1:
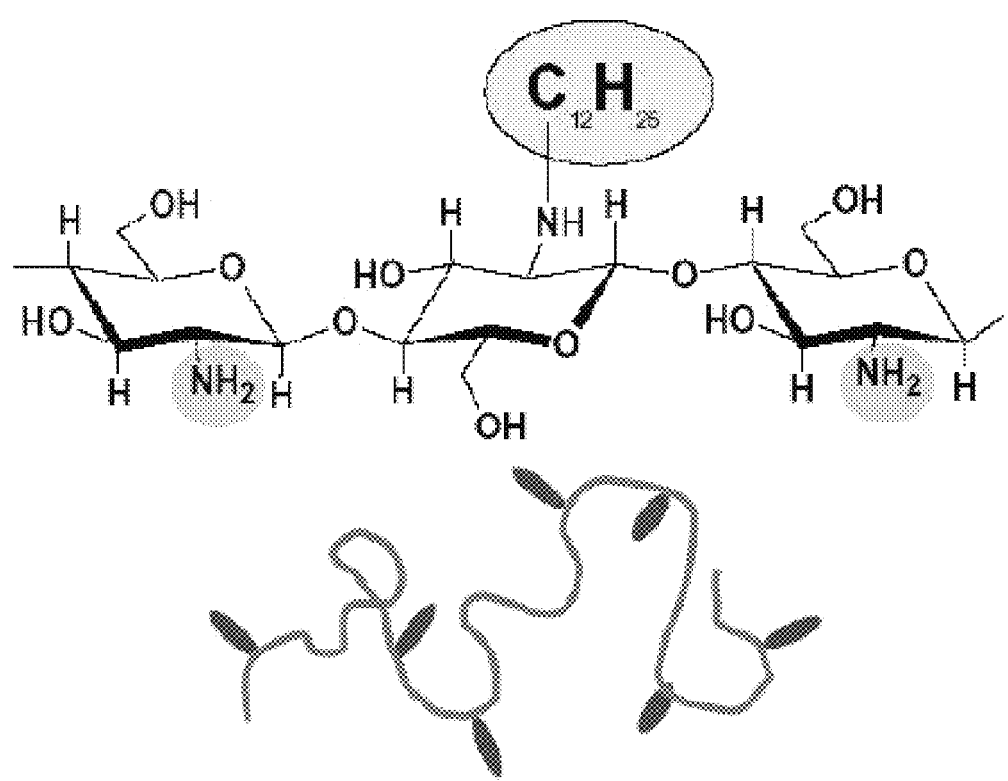
FIG. 1 is an image showing a chemical structure and a schematic of hydrophobically modified chitosan (HMC or HM-CS). The hm-chitosan "backbone" or "scaffold" is capable of binding with a plurality of hydrophobic substituents (shown as "$C_{12}H_{25}$").

In various aspects and embodiments, the present invention provides hemostatic products and methods for treating wounds, including surgical bleeds, cavity wounds and non-compressible hemorrhage. In various embodiments, the invention employs hydrophobically-modified polymer foams, gels, or pastes.

In one aspect, the invention involves a hydrophobically-modified polymer foam as a hemostatic product. For example, the hemostatic product may comprise a container having at least two compartments each containing a releasable, flowable solution. The first compartment comprises a solution of an acidified hydrophobically-modified polymer that creates hemostasis, for example, by forming a gel, artificial clot, or seal, in the presence of blood or bleeding injury. The second compartment comprises a solution of a bicarbonate or carbonate salt at an alkaline pH. Upon release of the contents through a mixing tip, the flowable products produce a stable foam (due to the production of $CO_2$) that will expand in a body cavity and produce a gel or "artificial clot" or seal with blood cells. The character and density of the hydrophobic grafts, and solution additives (including polymer additives), ensure the production of a stable foam. In some embodiments, the hydrophobic modifications comprise or consist essentially of linear hydrocarbon groups having a variable size.

In some embodiments, the foaming action of the product enables expansion of the material inside a body cavity (e.g., "expansion phase"), and during this expansion, the foam adheres and attaches to tissue in the body cavity, resulting in a halting of the bleeding during the expansion phase. In accordance with embodiments of the invention, varying the hydrophobic chain length of the hydrophobically-modified polymer, with select hydrophobic grafting densities, allows for production of a stable foam that does not quickly dissipate.

In some embodiments, the container is any type or shape that allows for controlled release and mixing of the contents, such as a double barrel syringe. The ratio of volume released in various embodiments can be from about 1:0.5 to 0.5:1 of the first and second containers. In some embodiments, the ratio of the solution volume in the first compartment and in the second compartment is about 1:1. In some embodiments, each compartment has a solution volume of from about 1 mL to about 100 mL, or from about 1 mL to about 50 mL. In some embodiments, each compartment has a solution volume of from about 10 mL to about 50 mL, or from about 20 mL to about 50 mL. In some embodiments, the product comprises a double-barrel syringe comprising two compartments and a static mixing tip.

In some embodiments, the linear hydrocarbon groups (or "grafts") are from about C6 to about C18, or are from about C8 to about C18. In some embodiments, the hydrophobically-modified polymer has hydrocarbon grafts of at least two different sizes attached to the polymer backbone. For example, the hydrocarbon grafts can comprise at least a first hydrocarbon chain length of from C8 to C12, which is sufficient to provide hemostatic properties, and at least a second hydrocarbon chain length of from C14 or greater, which provides improved blood gelling properties and foam integrity. In some embodiments, the second chain length is C16 or C18.

In some embodiments, the hydrophobically-modified polymer has hydrocarbon grafts of at least three different sizes attached to the polymer backbone. In some embodiments, the hydrophobic grafts comprise a combination of the following linear, saturated, hydrocarbon grafts: (a) grafts of C6 to C8 in length; (b) grafts of C10 to C14 in length; and (c) grafts of C16 to C18 in length. This combination of hydrocarbon grafts can provide strong blood gelling properties while also producing a stable foam. Further, the viscosity is amenable to dispensing through a double-barrel syringe. In various embodiments, the hydrophobically-modified polymer has a grafting density from about 1% to about 50% of the available functional groups on the polymer backbone. In some embodiments, particularly with regard to hm-chitosan, the hydrocarbon groups of (a) have a grafting density of about 3% to about 10% substitution of available amines (e.g., about 5 to 7% substitution of available amines). In some embodiments, the hydrocarbon groups of (b) have a grafting density of about 1% to about 5% substitution of available amines (e.g., from about 1% to 3% substitution of available amines), and the hydrocarbon groups of (c) have a grafting density of about 0.5 to about 3% substitution of available amines (e.g., about 1% substitution of available amines). In some embodiments, the chitosan is a medium molecular weight chitosan, having an average molecular weight (e.g., about 250 kDa), and level of de-acetylation as described below. In some embodiments, the hydrophobic grafts comprise C8 hydrocarbon groups, C12 hydrocarbon groups, and C16 hydrocarbon groups. In some embodiments, the linear hydrocarbon groups consist essentially of or consist of C8, C12, and C16 hydrocarbon groups. Generally, the ratios are selected to provide strong blood gelling properties (e.g., the gel can hold its weight for at least one hour), while enhancing foam integrity, and having a solution viscosity that can be easily dispensed from a double-barrel syringe. When employing alternative hydrophobically-modified polymers, equivalent grafting densities can be determined based on the availability of functional groups on the polymer backbone.

In some embodiments, hydrophobic grafts of C6 to C8 make up at least 50% of the hydrophobic grafts, and/or grafts of C16 to C18 make up no more than 20% or 15% of the hydrophobic grafts. In some embodiments, the hydrocarbon groups have a grafting density selected from samples X, Y, and Z from Table 1. As described, these samples exhibited strong gelation with blood, and the gel held its weight for a significant period of time (at least 3 hours) even with vial tapping. These materials suggest a unique property for treating non-compressible hemorrhage.

In some embodiments, the modified polymer is amphiphilic. In some embodiments, the polymer is based on a polysaccharide backbone, such as chitosan, alginate, gelatin, cellulosic, pectin, gellan gum, xanthan gum, dextran, and hyaluronic acid, among others. In some embodiments, the polymer is a synthetic (i.e., non-natural) polymer, such as polyethylene glycol, poly-lactic acid, poly-glycolic acid, poly lactic co-glycolic acid, poly lactic co-glycolic acid, polymethylmethacrylate, poly ¿-caprolactone, polyurethane, silicone, among others. In some embodiments, the polymer is hydrophobically-modified chitosan. In some embodiments, the polymer is hydrophobically-modified alginate. In some embodiments, the polymer is hydrophobically modified gelatin. In some embodiments, one or more compartments may comprise an unmodified polymer, including but not limited to chitosan, alginate, gelatin, pectin, dextran, polyethylene oxide, carboxymethylcellulose, hydroxyethylcellulose, hydropropylcellulose, and xanthum gum, among others.

The first compartment of the container contains an acidic solution of the hydrophobically-modified polymer, which is optionally a cationic polymer such as chitosan as described. In some embodiments, the principal solvent is water with an organic acid. The modified polymer (e.g., hm-chitosan) may be present in the first container at a concentration of from about 0.1 to about 5% by weight, or from about 1% to about 3% by weight, or in some embodiments about 2% by weight. The modified polymer may be formulated at a pH of from about 2.0 to 4.5, and in some embodiments is in the range of pH 3 to pH 4.5. In some embodiments, the organic acid is selected from one or more of acetic acid, lactic acid, ascorbic acid, and citric acid, and having a pH of from about 2 to about 4.5. For example, in the case of acetic acid and hm-chitosan, the acetic acid may be from 0.5M to 2M (e.g., about 1M).

In various embodiments, the hydrophobically-modified polymer solution has a viscosity (Pa·s) of about 0.5 to about 10, or a viscosity (Pa·s) of about 0.5 to about 5. In some embodiments, the viscosity (Pa·s) is from about 1 to about 5. The viscosity is low enough to allow the material to easily pass through the syringe.

The second compartment of the container comprises a solution of a carbonate or bicarbonate salt, such as a bicarbonate salt (e.g., sodium bicarbonate). In some embodiments, the bicarbonate solution is from about 0.5 to about 2M, or from about 0.7M to about 1.5M (e.g., about 1M). The bicarbonate or carbonate solution may be in the range of pH 8 to pH 14, or from about pH 8 to about pH 12. In some embodiments, the second compartment further comprises a polymer that acts to stabilize the foam, such as a polymer selected from gelatin, alginate, dextran, polyethylene oxide, hydroxyethylcellulose, and hydropropylcellulose, among others. In some embodiments, the second compartment comprises an anionic polymer (e.g. alginate or hm-alginate) and the first compartment comprises a cationic polymer (e.g., hm-chitosan as already described). Upon releasing the contents of the double barrel syringe, the contents will foam and form a coacervate. The coacervate contributes to the formation of a stable foam.

In exemplary embodiments, the first compartment comprises hydrophobically modified chitosan (as described), and the second compartment comprises hydrophobically modified alginate. Because the hm-chitosan will be cationic and the hm-alginate will be anionic, when combined upon release, the modified polymers will form a foam stabilizing coacervate. The hm alginate can be modified with hydrophobic grafts generally comprising hydrocarbon groups (e.g., alkyl groups), which can be independently selected from the range of C1 to C18 in various embodiments. In some embodiments, the hydrocarbon groups are independently selected from the range of C4 to C14, or independently selected from the range of C4 to C12. The hydrocarbon groups may be linear or branched, saturated or unsaturated, and may be variable in size. Exemplary hydrocarbon groups are linear, saturated, C6, C8, C10, and C12 hydrocarbon chains. The hydrocarbon groups or chains can be conjugated to carboxyl groups of the alginate backbone. For example, in various embodiments, from about 5% to about 50% of the carboxyl groups in the alginate backbone include a hydrophobic graft. In some embodiments, from about 10% to about 40% of the carboxyl groups in the alginate backbone have a hydrophobic graft. In some embodiments, the hydrophobically-modified alginate has C6, C8, and/or C10 hydrocarbon chains conjugated to from 10% to about 40% (e.g., about 25%) of the backbone carboxyl groups. In some embodiments, larger hydrophobic grafts are employed (i.e., larger than C10), and are conjugated to the polymer backbone at a density of less than about 15%, or less than about 10%, or less than about 5% (but at least about 1%) of the backbone carboxyl groups. Alternatively, the grafts may be smaller than C6, and conjugated to the polymer at a density of more than about 30%, or about 40%, or about 50% of the backbone carboxyl groups. In various embodiments, the hm-alginate (e.g., with C6 to C10 grafts as described) is present in the solution at 0.5 wt % to about 5 wt %, or at 1 wt % to about 3 wt % (e.g., about 2 wt %) of the solution.

In various embodiments, the first or second compartment further comprises one or more alternative or additional foam stabilizing additives. In some embodiments, the one or more foam stabilizing additives create flow resistance against blood that would otherwise enter the flowable product upon application to a bleeding site. In some embodiments, the additives comprise at least one of the following: hydrogel particles or granules (e.g., quaternized dimethylaminoethyl methacrylate (QDM)), dextran particles, polymers such as polyethylene oxide, and non-ionic surfactants. In some embodiments, the additive is polyethylene oxide. In some embodiments, the additive is a non-ionic surfactant, such as Pluronic 123. In some embodiments, the additive is a polymer, such as one or more selected from alginate, gelatin, pectin, dextran, hydroxyethylcellulose, hydroxypropylcellulose, carboxymethylcellulose, and xanthum gum. The additives can be added to either the first or second compartment, depending on their solubility at acidic or basic pH.

Blood gelation of the compositions disclosed herein can be evaluated using dynamic rheology, by perform a time-to-gelation evaluation. For example, dynamic time sweeps after foams are mixed with blood at equal volume. For treating severe bleeds, it is important to understand how quickly a hemostatic material can halt blood flow. Hm-chitosan solution and blood can be added to the rheometer stage sequentially. An oscillatory shear can then be actuated as quickly as possible to achieve the best representation of time-to-gelation. G' and G" are then recorded as a function of time, i.e., a "time sweep." Any time at which G' becomes higher than G" indicates a time-to-gelation point at which the material began acting more like an elastic solid, rather than a viscous liquid.

Tissue adhesion plays an important role for hemostatic materials which attempt to seal damaged tissue against a pressurized blood flow. The hydrophobic grafts on hm-chitosan are expected to attach and anchor onto fatty tissue and thereby improve adhesion to tissue relative to unmodified chitosan. This can be evaluated, for example, by examining the adhesion of solid foams to a bovine tissue using an automated strain-gauge. Based on rheological results, the number of grafted hydrophobes per chitosan chain are believed to be correlated with tissue adhesion.

As an exemplary means of testing tissue-material interaction, an adhesion test can be designed and developed from a standard tissue adhesion test.[4] For example, foams can be tested with an Instron machine, which involves placing a dry foam sample between a cover plate and loading platform. The foam can be mixed with 0.25 ml of bovine blood to coincide with in vivo large animal models. A 200 mm$^2$ PVC adhesion surface area can be brought into contact with the blood-foam mixture and loaded at a rate of 10 N/s to 10 N or kPa and held for 3 minutes. The adhesion-testing surface is then pulled away from the bandage at a rate of 1 mm/s, and the adhesion strength (kPa) can be determined by the maximum force divided by the contact surface area.

Upon mixing of the first compartment and the second compartment using the mixing tip, an expanding foam is generated due to stabilization of bubbles formed from the generation of $CO_2$ gas. In general, a smaller bubble size yields a longer drainage time, and therefore, longer stability. Foam stability (i.e., 'foamability') can be adjusted based on hydrophobic modification degrees and types, and also on the hydrophobically modified polymer's molecular weight. In addition, the static mixer foams of the present disclosure are able to form in situ, such that foam may be generated within the blood.

In another aspect, the invention provides a gel or paste based on a hydrophobically-modified polymer (as described above). The gel or paste can be based on single or variable-sized hydrophobic grafts as described above. In some embodiments, the gel or paste employs hydrophobically modified chitosan as described. In accordance with this aspect of the invention, hydrogel particles or granules, such as quaternized dimethylaminoethyl methacrylate (QDM) or dextran particles, are incorporated into the hydrophobically-modified polymer solution. In some embodiments, QDM is added at around 0.02 g/mL to about 0.1 g/mL, or from about 0.04 g/mL to about 0.075 g/mL (e.g., about 0.05 g/mL). In some embodiments, an amount of dextran particles is employed such that the resulting formulation comprises dextran particles at from about 0.1% by weight to about 2% by weight. In some embodiments, the formulation comprises dextran particles from about 0.1% to about 1.5% by weight, or from about 0.1% to about 1.0% by weight. In some embodiments, the formulation comprises dextran particles from about 0.5% to about 1.5% by weight, or from about 0.5% to about 1.0% by weight. For example, the formulation may comprise dextran particles at about 0.1% by weight; or about 0.2% by weight; or about 0.3% by weight; or about 0.4% by weight; or about 0.5% by weight; or about 0.6% by weight; or about 0.7% by weight; or about 0.8% by weight; or about 0.9% by weight; or about 1.0% by weight. The result will be a material with paste-like characteristics that is easy to handle and apply (e.g., during surgery). Further the material will create flow-resistance against blood that would enter the polymer matrix upon application to a bleeding site. In these embodiments, the hemostatic product is useful for treating minor soft tissue bleeds.

As disclosed herein, a product of the present disclosure may be used in methods related to treating a wound, including but not limited to non-compressible hemorrhage, cavity bleeds including soft tissue bleeds internal bleeding during surgery. In various embodiments, the wound is treated by releasing the contents of the product onto the site of bleeding. For example, the contents of the container may be released into one or more body cavities to halt a non-compressible hemorrhage. The contents of the container may also be released into one or more body cavities during surgery. In some embodiments, the flowable product expands by foaming action in the cavity. In some embodiments, the wound has high exudate or blood flow.

In some embodiments, the gel or paste employing hydrophobically-modified polymer is applied to a bleeding wound, such as a soft tissue bleed during surgery.

An exemplary hm-polymer material for use in accordance with embodiments of the invention is chitosan. Chitosan is the common name of the linear, random copolymer that consists of β-(1-4)-linked D-glucosamine and N-acetyl-D-glucosamine. The molecular structure of chitosan consists of a linear backbone linked with glycosidic bonds. Chitosan is the major component of crustacean shells such as crab, shrimp, krill and crawfish shells. Additionally, chitosan is the second most abundant natural biopolymer after cellulose. Commercial chitosan samples are typically prepared by chemical de-N-acetylation of chitin under alkaline conditions. Depending on the source of the natural chitin (extracted from shells) and its production process, chitosan can differ in size (average molecular weight Mw) and degree of N-acetylation (% DA). While the poor solubility of chitosan in water and in common organic solvents restricts its applications, reactive amino groups in the chitosan backbone make it possible to chemically conjugate chitosan with various molecules and to modulate its properties for use as a hemostatic product.

In various embodiments, the degree of deacetylation of chitin may range from about 40-100%, or in some embodiments, from 60 to 100%, or from 40 to about 90%, or from to about 100%, which determines the charge density. The structure of chitosan (deacetylated) is depicted in Formula 1:

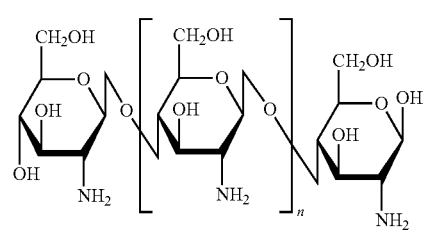

Formula 1

These repeating monomeric units include a free amino group, which makes molecules or compounds containing chitosan or its derivatives readily reactive. The hydrophobic modification of the chitosan backbone is through the association of an amphiphilic compound with the amino group, such that the hydrophobic tail of the amphiphilic compound is bound with the hydrophilic backbone structure. For determination of grafting density, the degree of acetylation is assumed to be about 85%.

The polymer that forms the backbone is chitosan, or similar polymer of synthetic or natural origin, including for example, water-soluble polysaccharides and water-soluble polypeptides. In some embodiments, the polymer is one or more hm-polysaccharides, including but not limited to cellulosics, chitosans, alginates, and gelatin, all of which are abundant, natural biopolymers. In some embodiments, the hm-biopolymer contains cationic groups.

The natural origin of these polysaccharides varies, cellulosics are found in plants, whereas chitosans and alginates are found in the exoskeleton or outer membrane of a variety of living organisms. Many of these naturally occurring polymers, in addition to being able to form long stable chains for forming the polymer backbone, have properties that are beneficial for a hemostat application, including anti-microbial properties.

In some embodiments, the hm-chitosan is derived from a deacteylated chitin, which may be derived from one or more of crab, shrimp, krill, and crawfish.

The form of the natural polymers used may vary to include standard states, derivatives and other various formulations. For example, the hm-cellulosics may be formed from, without limitation, hydroxyethyl cellulose, hydroxypropyl cellulose, methyl cellulose, hydroxypropyl methyl cellulose, and/or hydroethyl methyl cellulose. Hm-chitosans may be prepared from, without limitation, the following chitosan salts: chitosan lactate, chitosan salicylate, chitosan pyrrolidone carboxylate, chitosan itaconate, chitosan niacinate, chitosan formate, chitosan acetate, chitosan gallate, chitosan glutamate, chitosan maleate, chitosan aspartate, chitosan glycolate and quaternary amine substituted chitosan and salts thereof. Hm-alginates may be prepared from, without limitation, sodium alginate, potassium alginate, magnesium alginate, calcium alginate, and/or aluminum alginate. It is to be understood that various other forms of any of these natural polysaccharides that provide the proper functional capabilities may be employed without departing from the scope and spirit of the present invention.

In some embodiments, the polymeric component is a mixture of polysaccharides. For instance, the mixture may be of various different sub-classes of a single polymer class. Alternatively, the mixture may include two or more different classes of polymer, for instance a chitosan and an alginate.

In various embodiments, the biopolymer is an hm-chitosan, which may be prepared according to International PCT Application No. PCT/US18/25742, which is hereby incorporated by reference in its entirety.

In some embodiments, the molecular weight of the polysaccharides used as the biopolymer range from about 25,000 to about 1,500,000 grams per mole. In various embodiments, the molecular weight of the biopolymer ranges from about 40,000 to about 500,000 grams per mole, or from about 50,000 to about 250,000 grams per mole, or from about 50,000 to about 100,000 grams per mole. In some embodiments, the chitosan has an average molecular weight of from 200,000 to 300,000 grams per mole (e.g., about 250,000 grams per mole). As used herein, the term "molecular weight" means average molecular weight. Methods for determining average molecular weight of bio-polymers include low angle laser light scattering (LLS) and Size Exclusion Chromatography (SEC). In performing low angle LLS, a dilute solution of the polysaccharide, typically 2% or less, is placed in the path of a monochromatic laser. Light scattered from the sample hits the detector, which is positioned at a low angle relative to the laser source. Fluctuation in scattered light over time is correlated with the average molecular weight of the polysaccharide in solution. In performing SEC measurements, again a dilute solution of biopolymer, typically 2% or less, is injected into a packed column. The polysaccharide is separated based on the size of the dissolved polymer molecules and compared with a series of standards to derive the molecular weight.

The biopolymer (such as chitosan) backbone includes a hydrophilically reactive functional group (e.g., amino groups) that binds with the hydrophilically reactive head groups (e.g., carbonyl functional group) of an amphiphilic compound (e.g., aldehyde), to form the hm-chitosan or other hm-polymer. The head group is further associated with a hydrophobic tail group. In the current embodiment, the hydrophobic tail may be, for example, a hydrocarbon. Thus, a hydrophobic tail is associated with the biopolymer backbone providing the hydrophobic modification to the molecule that extends from the backbone and may interact with a surrounding environment in numerous ways, such as through hydrophobic interaction with materials. Examples of procedures for modifying polymers are as follows.

Alginates can be hydrophobically modified by exchanging their positively charged counterions (e.g. Na+) with tertiary-butyl ammonium (TBA) ions using a sulfonated ion exchange resin. The resulting TBA-alginate is dissolved in dimethylsulfoxide (DMSO) where reaction occurs between alkyl (or aryl) bromides and the carboxylate groups along the alginate backbone. Alginate can also be modified by fatty amine groups (e.g. dodecyl amine), followed by addition of 1-ethyl-3-(3-dimethylaminopropyl) carbodiimide, via EDC coupling.

Cellulosics can be hydrophobically modified by first treating the cellulosic material with a large excess highly basic aqueous solution (e.g. 20 wt % sodium hydroxide in water). The alkali cellulose is then removed from solution and vigorously mixed with an emulsifying solution (for example, oleic acid) containing the reactant, which is an alkyl (or aryl) halide (e.g. dodecyl bromide).

Chitosans can be hydrophobically modified by reaction of alkyl (or aryl) aldehydes with primary amine groups along the chitosan backbone in a 50/50 (v/v) % of aqueous 0.2 M acetic acid and ethanol. After reaction, the resulting Schiff bases, or imine groups, are reduced to stable secondary amines by dropwise addition of the reducing agent sodium cyanoborohydride.

Alternatively, fatty acid anhydride chemistry may be used for hydrophobic modification of chitosan, resulting in amide bonds with the chitosan polymer and the hydrocarbon chains. While hydrolysis of amide bonds is generally known to occur in the presence of dilute acids, which acts as a catalyst for the reaction between the amide and water, the amide bonds formed between chitosan and alkyl anhydrides are shelf stable, even in the presence of dilute acids that are required to maintain solubility of the hydrophobically-modified chitosan. Accordingly, the modified polymers may be prepared using a one-pot synthesis, without the need for harsh reagents, including reducing agents. The materials can be precipitated following the reaction and dried for processing and incorporation into products, including solutions, gels, and foams, among others.

The degree of substitution of the hydrophobic substituents on the polymer is up to 50% of available functional groups, for example, amines in the case of chitosan. For example, in some embodiments, the hydrophobic substituents can be added to from 1 to 50% of available amines, or from 10 to 50% of available amines, or from 20 to 50% of available amines. In some embodiments, the grafting density is no more than about 15% of available amines.

In some embodiments, the hydrophobic substituent is derived from an amphiphilic compound, meaning it is composed of a hydrophilic Head group and a hydrophobic Tail group. The Head group binds with the polymer and positions the Tail group to extend from the backbone of the polymer scaffold. This makes the hydrophobic Tail group available for hydrophobic interactions. The Tail group is a hydrocarbon of various forms.

The hydrophobic Tail group of the amphiphilic compound bound to the polymer backbone of the current invention is capable of branching and/or allowing the inclusion of side chains onto its carbon backbone. It may be understood that the strength of the hydrophobic interaction is based upon the available amount of "hydrophobes" that may interact amongst themselves or one another. Thus, it may further promote the hydrophobic effect by increasing the amount of and/or hydrophobic nature of the hydrophobic Tail group that is interacting. For instance, a hydrophobic Tail group, which in its original form may include a hydrocarbon chain, may promote an increase in its hydrophobicity (ability to hydrophobically bond and strength of hydrophobic interaction) by having a hydrophobic side chain attach to one of the carbons of its carbon backbone.

In some embodiments, the current invention contemplates the use of various molecules and/or compounds that may increase hemorrhage control, durability, water repellent properties, and/or flexibility of the hemostat product. The side chains may be linear chains, aromatic, aliphatic, cyclic, polycyclic, or any various other types of hydrophobic side chains as contemplated by those skilled in the art.

As used herein, the term "about" means±10% of the associated numerical value.

Any aspect or embodiment described herein can be combined with any other aspect or embodiment as disclosed herein.

Other aspects and embodiments of the invention will be apparent to the skilled artisan from this disclosure.

The invention will be further described in the following examples, which do not limit the scope of the invention described in the claims.

EXAMPLES

Disclosed herein are compositions and methods related to variable-length hydrophobically-modified polymers comprising hydrophobes that can effectively treat a non-compressible hemorrhage in a patient. The compositions and methods of the present disclosure are capable of promoting hemostasis and/or a hemostatic response through the interaction of the hydrophobes with cells and/or tissue.

One key feature of the material composition is the attachment of hydrophobes (e.g., nano-scale sized "stickers") along the backbone of chitosan chains. The top of FIG. 1 shows the chemical structure hydrophobically modified (hm)-chitosan, and the bottom of FIG. 1 illustrates a chain of hm-chitosan (HMC). While chitosan itself can be used as a hemostat in several commercial bandages, the hm-chitosan composition has a significantly enhanced efficacy for stopping bleeds relative to the native form of the biopolymer.[1] It is the action of the hydrophobes that allows the polymer to "grip" blood cells and soft tissue cells in a reversible fashion. Without wishing to be bound by theory, the hydrophobes orchestrate the self-assembly of the polymer into a 3-dimensional elastic network barrier upon contact with blood cells.

Figure 2:
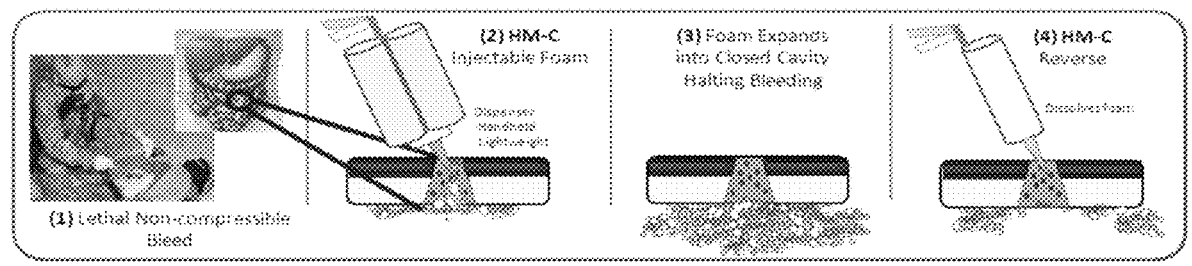
FIG. 2 illustrates the concept of an injectable HMC foam for treatment of a non-compressible hemorrhage. The foam is injected into a cavity having a non-compressible bleed. The foam expands into the cavity, and the gelation of the polymer with blood halts bleeding. A reversal agent comprising cyclodextrin can reverse the gelation.

FIG. 2 shows an injectable hm-chitosan foam for reversible treatment of a non-compressible hemorrhage. As shown in FIG. 2, the foam-based hemostat may be injected into a closed cavity from a handheld, lightweight double-barrel syringe (e.g., "caulk gun" style delivery). This method of delivery can be particularly useful for treating non-compressible hemorrhage, i.e., bleeding which is not accessible to direct pressure. While several advanced hemostatic devices (i.e., products which stop bleeding) have been developed over the last decade to offer improved patient outcomes over the perennial Army Field Dressing (Cotton Gauze), none of the hemostatic devices are robustly suited to treat a non-compressible hemorrhage on the field. In the experiments of the present disclosure, it was hypothesized that the foaming action would allow the material to expand into a damaged body cavity while also adhering to a tissue or cell, thereby stopping the bleeding during the expansion process. As shown in FIG. 2 ("HM-C Reverse"), the resulting gel barrier could then be easily removed by a provider (e.g., a trauma surgeon) using a flowable product that reverses the gelation. See U.S. Pat. No. 8,664,199, which is hereby incorporated by reference in its entirety.

Example 1: Characterization and Synthesis of a Series of Hydrophobically-Modified (hm)-Chitosans Varying in Both Hydrophobe Grafting Density and Hydrophobe Length Blood can be gelled upon mixing with hm-chitosan.[2] Further studies on the effect of level of hydrophobic grafting density or hydrophobic chain length (i.e. the hydrophobic design) have been limited with regard to blood gelling ability. Changing variables for an amphiphilic polymer (i.e., a polymer containing both hydrophilic and hydrophobic segments) can significantly alter the phase behavior of the polymer. As such, these variables were viewed as optimization levers for the development of a foam material that functions via self-assembly in biological fluid. The experiments of this example sought to understand the effects of varying the components of hm-chitosan as they relate to blood gelation and tissue adherence.

Synthesis of hm-Chitosans

The following variants of hm-Chitosan (Chitosan Source: Primex, Medium MW) were synthesized in 2 g batches. Hm-chitosan was synthesized by attaching acyl groups to the chitosan backbone via reaction with a range of fatty anhydrides (from C8 to C18 chain length). Briefly, 1 wt % chitosan solution was dissolved in 0.2 M Acetic Acid in water and 50% (v/v) ethanol. Under stirring, the fatty anhydride was added to the reaction mixture, forming an N-acylated attachment at the —$NH_2$ position of the chitosan backbone. Grafting density was determined by the percentage of available amines along the chitosan backbone on a molar basis. The reaction was left to stir overnight, and the chitosan was then precipitated from solution by adding 0.1 M NaOH dropwise. The precipitates (e.g., fatty acids of the corresponding chain length of the utilized fatty anhydride group) were washed 5× with ethanol and 5× with water to ensure sample purification from excess reactants. In the above reaction synthesis of hm-Chitosan, for example, palmitoyl anhydride yields palmitic acid hydrophobic grafts.

Table 1 below shows a selected list of synthesized hm-Chitosan batches. Sample A in Table 1 is unmodified, or can be referred to as native chitosan. All other lettered samples in Table 1 (left column) have at least some degree of hydrophobic modification. Hence, Sample A acts an important control in the experiments of this disclosure.

TABLE 1

Selected List Of HM-Chitosan Batches Synthesized

| Sample | Chitosan Source | Graft type | Order of Variable Length | Grafting Density (theoretical % mol) |
|---|---|---|---|---|
| A | Primex | none | 0° | 0 |
| B | Primex | C-12 | 1° | 1 |
| C | Primex | C-14 | 1° | 1 |
| D | Primex | C-16 | 1° | 1 |
| E | Primex | C-18 | 1° | 1 |
| F | Primex | C-10 | 1° | 5 |
| G | Primex | C-12 | 1° | 5 |
| H | Primex | C-14 | 1° | 5 |
| I | Primex | C-16 | 1° | 5 |
| J | Primex | C-8 | 1° | 10 |
| K | Primex | C-10 | 1° | 10 |
| L | Primex | C-12 | 1° | 10 |
| M | Primex | C-14 | 1° | 10 |
| N | Primex | C-8, C-14 | 2° | 10.1 |
| O | Primex | C-8, C-16 | 2° | 10.1 |
| P | Primex | C-8, C-18 | 2° | 10.1 |
| Q | Primex | C-10, C-14 | 2° | 2.5, 1 |
| R | Primex | C-10, C-16 | 2° | 2.5, 1 |
| S | Primex | C-10, C-18 | 2° | 2.5, 1 |
| T | Primex | C-12, C-14 | 2° | 2.5, 1 |
| U | Primex | C-12, C-16 | 2° | 2.5, 1 |
| V | Primex | C-12, C-18 | 2° | 2.5, 1 |
| W | Primex | C-8, C-12, C-16 | 3° | 3, 1, 1 |
| X | Primex | C-8, C-12, C-16 | 3° | 3, 3, 1 |

TABLE 1-continued

Selected List Of HM-Chitosan Batches Synthesized

| Sample | Chitosan Source | Graft type | Order of Variable Length | Grafting Density (theoretical % mol) |
|---|---|---|---|---|
| Y | Primex | C-8, C-12, C-16 | 3° | 5, 1, 1 |
| Z | Primex | C-8, C-12, C-16 | 3° | 5, 3, 1 |

In total, 120 HMC variants were synthesized. The above 25 HMC samples listed in Table were studied due to a pre-screening of blood gelation scoring (see Table 2 below). Only samples with a score of 3 or higher were selected for follow up characterization. In Table below, visual blood gelation scores of 0 to 5 were given to each sample according to the following scale after mixing an HMC solution (1.5 wt % in 0.1 M acetic acid) with blood (citrated bovine blood (Lampire)) at 2:1 polymer: blood ratio using a vortex mixer for about second. Samples X, Y, and Z, which have a range of hydrophobic graft lengths between C8 and C16, and a theoretical grafting density of between 7-9% mol (i.e., substitution of 7-9% of available amines), displayed very strong blood gelation.

TABLE 2

Visual Blood Gelation Scores Of HMC Batches Synthesized

| Sample | Visual Blood Gelation Score |
|---|---|
| A | 0 |
| B | 3 |
| C | 3 |
| D | 3 |
| E | 3 |
| F | 3 |
| G | 4 |
| H | 4 |
| I | 4 |
| J | 3 |
| K | 3 |
| L | 4 |
| M | 4 |
| N | 3 |
| O | 3 |
| P | 4 |
| Q | 4 |
| R | 4 |
| S | 4 |
| T | 3 |
| U | 4 |
| V | 4 |
| W | 4 |
| X | 5 |
| Y | 5 |
| Z | 5 |

Visual Blood Gelation Scale

0=freely flowing, no gelation at all;
1=still freely flowing, slight increase in viscosity;
2=still freely flowing, significant increase in viscosity;
3=mild gelation and then initial gelation, quickly followed by flowing; does not hold weight upon tapping the vial;
4=moderate gelation, and then the gel holds weight for significant period of time, even with tapping the vial; flows again within 1 hour of gelation;
5=strong gelation, and then the gel holds weight for significant period of time, even with tapping the vial; holds weight for greater than 3 hours after initial gelation.

Example 2: $^1$H-NMR Characterizations of Hm-Chitosans and Determination of the Strength of Hydrophobic Interactions of Synthesized Hm-Chitosans with Blood and Tissue In Vitro The experiments of this example sought to further understand the result of the synthesis on an analytical chemical level. Hydrophobic modification of chitosan is best characterized in a quantitative chemical sense with $^1$H-NMR as the hydrogen molecules along the grafted hydrocarbon backbone will have a distinctly different resonance than those normally attached to the chitosan backbone.

Experimental Design and Results

Figure 3A:
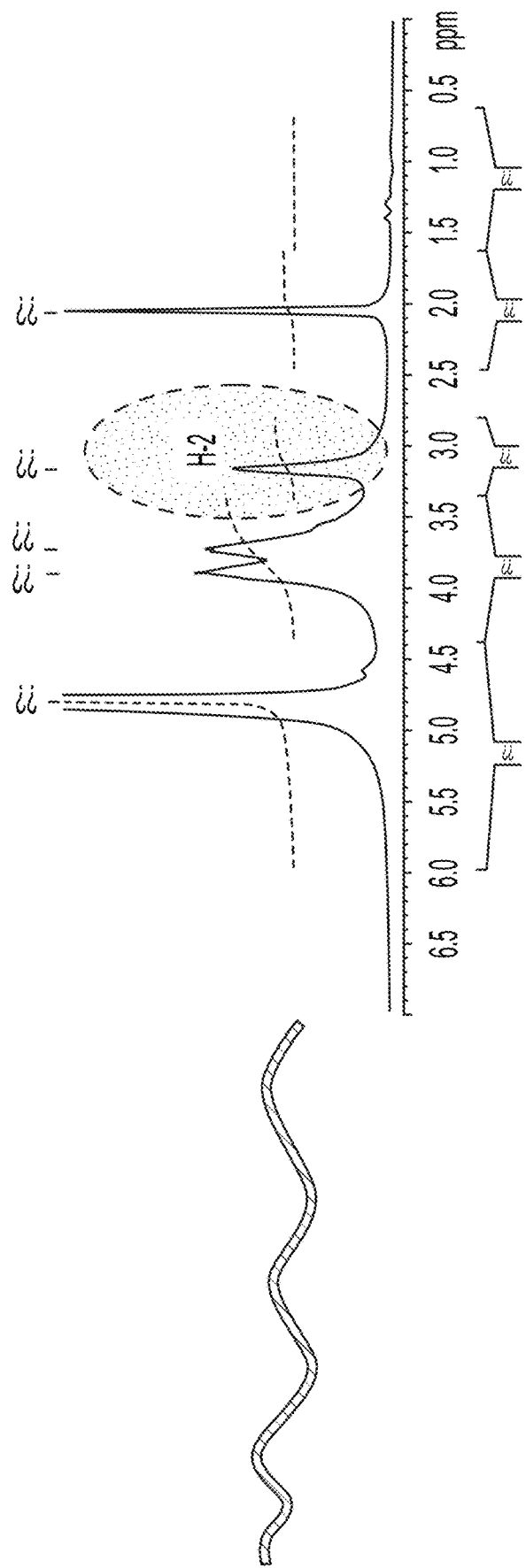
FIG. 3A-B shows an example of a 1H-NMR Spectra of (a) Native Chitosan (FIG. 3A) and (b) HM-Chitosan (FIG. 3B). The key peaks involved in calculating the hydrophobe grafting density are highlighted.
Figure 3B:
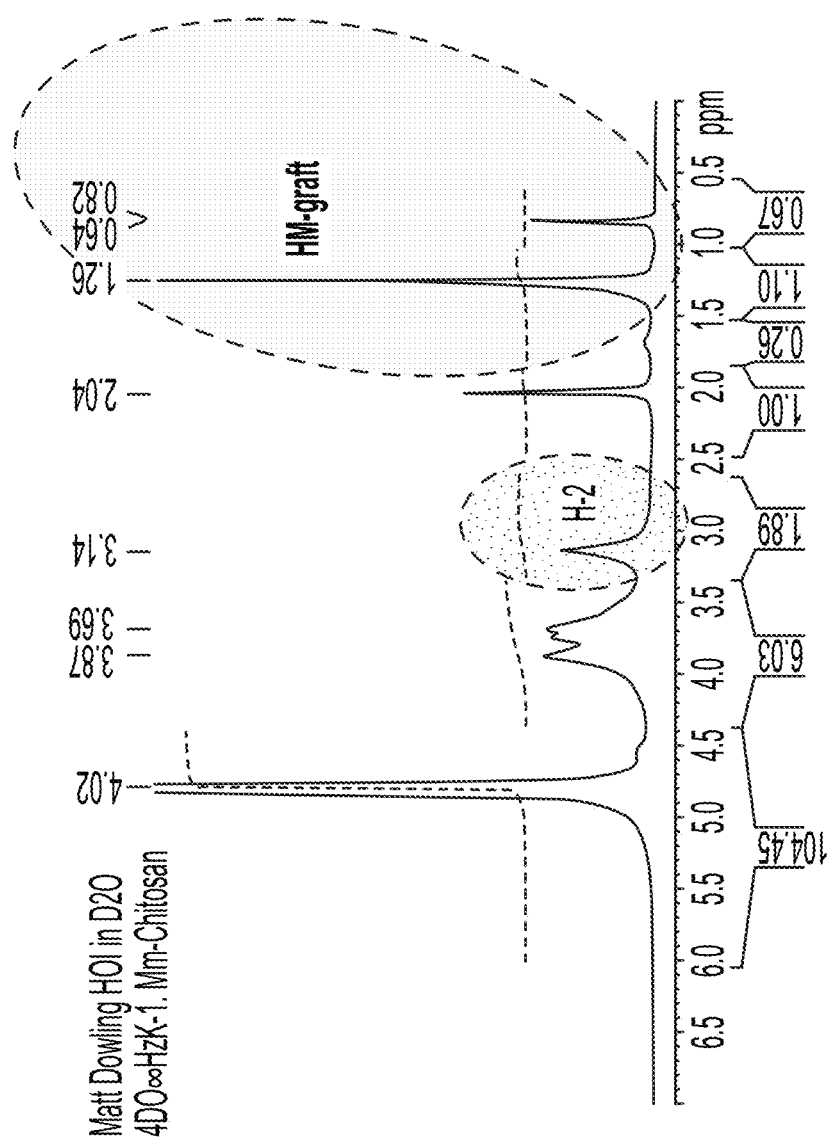
Figure 3B:

Synthesized hm-chitosans were dissolved in 0.2 M $CD_3COOD$ in $D_2O$ and submitted to the NMR facility at the University of Maryland for $^1$H-NMR characterization. Calculation of the actual degrees of graft substituted depended upon peak integrals for the H-2 hydrogen (present on every monomer unit, chemical shift δ ~3.1 ppm), and the graft hydrogens (chemical shift δ ~1.25 ppm). FIG. 3A-B shows an example spectra of native (FIG. 3A) and modified (FIG. 3B) chitosan to highlight the key peaks involved in calculating the hydrophobe grafting density.

Table 3 shown below displays key $^1$H-NMR data and analysis on all synthesized samples. The reactions for the C-12 grafts generated relatively low deviations from theoretically expected results relative to the C-18 grafts. The large deviations from expected degree of substitution values for the C-18 hm-chitosans may be attributed to low solubility during reaction. Aside from C-18 grafts, the modifications to the chitosan backbone were fairly close to theoretical values. This gives assurance that hydrophobic modification did occur, and the experiments of this example provide a mechanism of comparing real versus theoretical values of hydrophobic modification.

TABLE 3

$^1$H-NMR Characterization Summary Of Synthesized hm-Chitosan Batches

| Sample | Graft(s) | [H-2] Peak Integral (δ~ 3.1 ppm) | [Graft] Peak Integral(s) (δ~ 1.25 ppm) | Degree(s) of Substitution (actual % mol) | Degree (s) of Substitution (theoretical % mol) | % Deviation(s) |
|---|---|---|---|---|---|---|
| A | none | 16.75 | 0 | 0.00 | 0 | N/A |
| B | C-12 | 14.54 | 3.75 | 1.03 | 1 | +3.07 |
| C | C-14 | 15.32 | 4.65 | 1.05 | 1 | +4.46 |
| D | C-16 | 16.19 | 6.1 | 1.14 | 1 | +12.41 |
| E | C-18 | 13.75 | 4.55 | 0.89 | 1 | −11.81 |
| F | C-10 | 17.55 | 17.18 | 4.66 | 5 | −7.26 |

TABLE 3-continued

¹H-NMR Characterization Summary Of Synthesized hm-Chitosan Batches

| Sample | Graft(s) | [H-2] Peak Integral (δ= 3.1 ppm) | [Graft] Peak Integral(s) (δ= 1.25 ppm) | Degree(s) of Substitution (actual % mol) | Degree (s) of Substitution (theoretical % mol) | % Deviation(s) |
|---|---|---|---|---|---|---|
| G | C-12 | 17.15 | 24.24 | 5.65 | 5 | +11.56 |
| H | C-14 | 15.98 | 25.36 | 5.47 | 5 | +8.63 |
| I | C-16 | 14.67 | 23.56 | 4.87 | 5 | −2.74 |
| J | C-8 | 15.33 | 26.75 | 10.26 | 10 | +2.58 |
| K | C-10 | 15.76 | 31.55 | 9.53 | 10 | −4.90 |
| L | C-12 | 17.11 | 42.95 | 10.04 | 10 | +0.41 |
| M | C-14 | 18.16 | 48.91 | 9.29 | 10 | −7.68 |
| N | C-8, C-14 | 13.64 | 25.54, 4.95 | 11.01, 1.25 | 10, 1 | +9.21, +20.01 |
| O | C-8, C-16 | 14.48 | 23.45, 4.66 | 9.53, 0.98 | 10, 1 | −4.97, −2.54 |
| P | C-8, C-18 | 14.94 | 24.75, 5.11 | 9.74, 0.92 | 10, 1 | −2.62, −8.39 |
| Q | C-10, C-14 | 15.88 | 8.31, 5.03 | 2.49, 1.09 | 2.5, 1 | −0.45, +8.45 |
| R | C-10, C-16 | 15.01 | 8.19, 4.75 | 2.60, 0.96 | 2.5, 1 | +3.90, −4.28 |
| S | C-10, C-18 | 14.78 | 7.91, 5.17 | 2.55, 0.95 | 2.5, 1 | +1.78, −5.78 |
| T | C-12, C-14 | 16.72 | 10.44, 4.34 | 2.50, 0.90 | 2.5, 1 | −0.10, −11.72 |
| U | C-12, C-16 | 16.02 | 10.75, 5.22 | 2.68, 0.99 | 2.5, 1 | +6.86, −1.28 |
| V | C-12, C-18 | 17.13 | 11.11, 5.25 | 2.59, 0.83 | 2.5, 1 | +3.63, −20.73 |
| W | C-8, C-12, C-16 | 16.54 | 9.23, 4.22, 6.01 | 3.28, 1.02, 1.10 | 3, 1, 1 | +8.61, +2.01, +9.18 |
| X | C-8, C-12, C-16 | 17.82 | 8.47, 13.25, 5.51 | 2.80, 2.97, 0.94 | 3, 3, 1 | −7.30, −0.87, −6.73 |
| Y | C-8, C-12, C-16 | 14.43 | 13.77, 3.78, 4.75 | 5.61, 1.05, 1.01 | 5, 1, 1 | +10.93, +4.56, −0.25 |
| Z | C-8, C-12, C-16 | 13.92 | 12.45, 9.22, 5.89 | 5.26, 2.65, 1.28 | 5, 3, 1 | +4.96, −13.23, +22.01 |

Example 3: Rheological Characterizations of hm-Chitosans

The experiments of this example were based on dynamic and steady state rheology profiling on foams created from a double-barrel delivery device.

Rheology is a useful method to understand how viscoelastic materials behave under shear stress. This a particularly fitting characterization method for hydrophobically modified polymers, as addition of hydrophobes to the backbone of the polymer increases the viscosity of the resulting solution. Hence, rheology is a relatively efficient way of determining trends in the solution properties of amphiphilic polymers.

Experimental Design and Results

Steady and dynamic rheological experiments were performed on a Rheometrics AR2000 stress-controlled rheometer. A cone-and-plate geometry of 40 mm diameter and a 4° cone angle was used and samples (1 wt % in solution, 0.2M acetic acid) were run at the physiological temperature of 37° C. Dynamic frequency spectra were obtained in the linear viscoelastic regime of the samples, as determined from dynamic strain sweep experiments. Frequency sweeps of all samples displayed fluid-like mechanical properties with G" (viscous modulus)>G' (elastic modulus) for a practical range of frequencies, with both being strong functions of frequency. This is an important gating criterion for the experiments of this example as the samples must be able to flow through the double barrel syringe in order to be delivered into a bleeding cavity. A comparison of apparent viscosities ($\eta$ (Pa·s)) of all samples is shown in Table 4 below.

TABLE 4

Zero-Shear Viscosities Of Synthesized Hm-Chitosan Batches

| Sample | Zero Shear Viscosity (Pa-s) |
|---|---|
| A | 0.021 |
| B | 0.45 |
| C | 0.72 |
| D | 1.35 |
| E | 2.11 |
| F | 0.68 |
| G | 1.45 |
| H | 1.87 |
| I | 5.15 |
| J | 0.55 |
| K | 1.22 |
| L | 4.53 |
| M | 13.12 |
| N | 1.01 |
| O | 2.13 |
| P | 4.96 |
| Q | 0.85 |
| R | 2.02 |
| S | 3.52 |
| T | 0.85 |
| U | 2.45 |
| V | 3.14 |
| W | 0.71 |
| X | 2.68 |
| Y | 0.93 |
| Z | 3.27 |

The apparent viscosities are amenable to the double barrel syringe foam concept.

Figure 4:
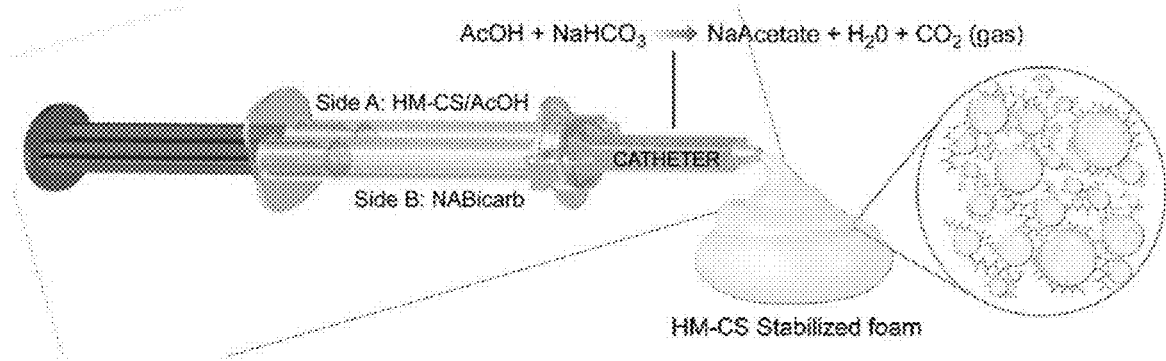
FIG. 4 is an image showing a double barrel syringe producing HM-CS foam. One barrel contains HM-CS in acidic solution, and the second barrel contains sodium bicarbonate. Upon dispensing the solutions through a mixing catheter, the reaction between sodium bicarbonate and the acidic solution produces a foam due to the generation of $CO_2$. The character of the HM-CS hydrophobic grafts and formulation additives can stabilize the HM-CS foam to prevent immediate or quick dissipation, and ensure sufficient foam integrity.

In Vitro Characterization of Foams Created from Double-Barrel Delivery Device when Mixed with Blood at Equal Volume of Foam Chitosan samples were loaded into double barrel syringes at 2 wt % in 1M Acetic Acid (with 1M Sodium Bicarbonate in the adjacent barrel), and were mixed with heparinized bovine blood at a ratio of 50:50 v/v, resulting in final mixture concentrations of 0.5 wt % polymer and 50% blood. All samples studied in this rheology series had a polymer concentration of 0.5 wt % and a blood concentration of 50% by volume. Thus, as an example, "Sample C" in this results section describes a mixture of 0.5 wt % of Sample C and 50% blood by volume. FIG. 4 shows an illustration of the double barrel syringes used for the experiments of this example.

As previously described above, a Rheometrics AR2000 stress-controlled rheometer was used to test the mixtures under the same testing parameters as described above. Steady shear rheology testing results from this set of samples is shown in Table 5 below. It is important to note the viscosity values recorded for Sample A (unmodified chitosan+blood) over the studied range stress values. Sample A displays an "apparent viscosity" (i.e., viscosity as shear stress approaches 0) of $10^{-2}$ Pa·s, which is about 10 times the viscosity of water. In contrast, Sample G and Sample Z show apparent viscosity values on the order of $10^3$ and $10^4$ Pa·s, respectively. For Sample Z, this represents a million-fold increase in apparent viscosity relative to Sample A, and for Sample G, this represents a hundred-thousand-fold increase in apparent viscosity. Visually, both Samples G and Z held their own weight upon vial inversion, whereas Sample A remained a freely-flowing viscous liquid. Samples B, C, D, E, J, K, N, O and T each displayed similar apparent viscosities on the order of $10^2$, which represent a ten thousand-fold increase in viscosity relative to Sample A. Visually, samples B, C, D, E, J, K, N, O and T showed a large increase in viscosity, but soon after gelation, the sample would begin to flow again. This result suggests that level of hydrophobicity of the chitosan backbone, assuming the same hydrophobe type, positively correlates with its ability to gel blood. However, by varying the hydrophobe length, even stronger gelation was achieved even with a lower grafting density.

TABLE 5

Zero-Shear Viscosities Of HM-Chitosan Foams Mixed With Blood

| Sample | Zero Shear Viscosity (Pa-s) |
| --- | --- |
| A | 0.075 |
| B | 95.15 |
| C | 147.12 |
| D | 152.88 |
| E | 275.01 |
| F | 468.71 |
| G | 1,212.56 |
| H | 1,225.24 |
| I | 1,281.44 |
| J | 267.33 |
| K | 371.89 |
| L | 1,152.67 |
| M | 1,207.13 |
| N | 381.45 |
| O | 489.43 |
| P | 1,313.78 |
| Q | 1,322.56 |
| R | 1,345.51 |
| S | 1,412.47 |
| T | 591.05 |
| U | 1,352.87 |
| V | 1,446.79 |
| W | 2,461.31 |
| X | 7,812.14 |
| Y | 8,981.65 |
| Z | 9,104.33 |

Figure 5A:
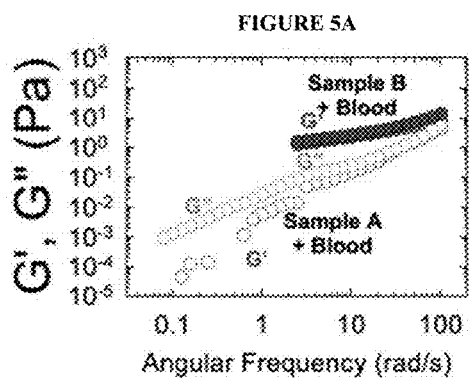
FIG. 5A-E are graphs of a Dynamic Rheology of Chitosan-Blood Mixtures. The graphs are labelled (a), (b), (c), (d), and (e), respectively. The samples are described in Table 1. Sample (a) is an unmodified, or native, chitosan (FIG. 5A). Samples (b), (c), (d), and (e) have varying degrees and character of hydrophobic modification (FIG. 4B-E).
Figure 5B:
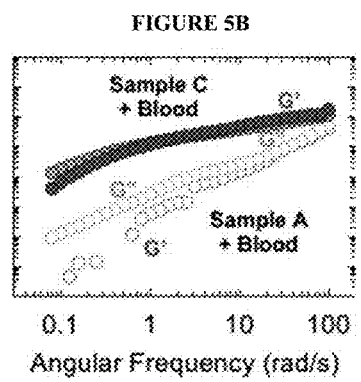
Figure 5C:
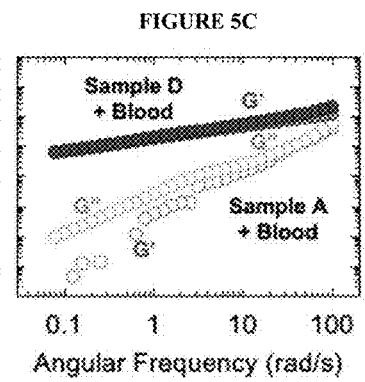
Figure 5D:
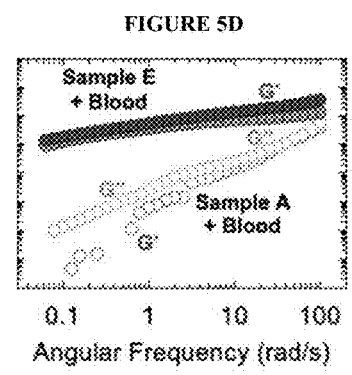
Figure 5E:
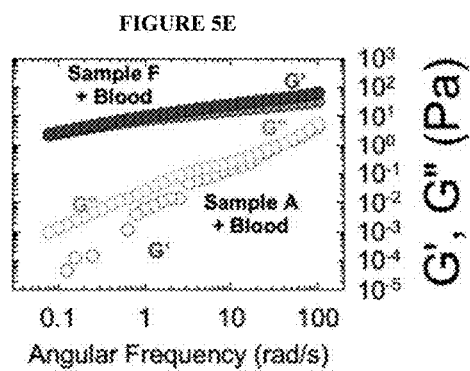

A portion of this set of samples mixed with blood underwent dynamic rheology testing in order to understand their behavior over a range of timescales. FIG. 5A-E displays the data from dynamic rheology (oscillatory shear), which probes the linear viscoelastic response of the samples. The data plotted represents the elastic ((G') and viscous (G") moduli as functions of the angular frequency, i.e., the inverse of time, and as such, they supply us with time-based information about the material's behavior. In each graph of FIG. 5 (FIG. 5A, FIG. 5B, FIG. 5C, FIG. 5D, and FIG. 5E), the frequency sweep (moduli vs. oscillatory shear frequency) of Sample A, native chitosan, is displayed for contrast purposes. It was observed that Sample A displays a viscous response: both its moduli decrease sharply with frequency and its G" (open green circles) exceeds (G' (open red circles) over the frequency range. This result is expected from the visual characteristics of the chitosan/blood (Sample A) mixture. In contrast, all hm-chitosan and blood samples display G' values (closed red circles) which exceed G" values (closed green circles) over the majority of the frequency range, with relatively low dependence on angular frequency. However, there are distinct differences among Samples B, C, D, E, and F. In FIG. 5A, G' and G" values of Sample B are increased only slightly relative to Sample A values. In FIG. 5B, the G' and G" values of Sample C are more significantly increased relative to Sample A; however, there is a crossover of G' and G" at ~1 rad/s, indicating that the sample becomes liquid-like over longer timescales. In FIG. 5C, FIG. 5D, and FIG. 5E, it was observed that G' and G" for Samples D, E and F are significantly increased relative to Sample A, and the mixtures show largely elastic response typical of a physical gel: note that G' exceeds G" over the entire frequency range and moreover, both moduli are weakly dependent on frequency. The weak frequency dependence of the moduli is indicative of a sample-spanning network that is able to store the shear deformation; relaxation of this network occurs very slowly over long time scales. These dynamic rheology findings support the steady shear results which show that chitosan samples with a higher degree of hydrophobic modification tend to form stronger gels upon mixing with blood. Although, as shown in FIG. 4, hm-chitosans with too much hydrophobic character (e.g. Sample G) are not useful as a flowable sealant, as they become extremely viscous and at certain levels of modification are no longer be water-soluble.

Figure 6:
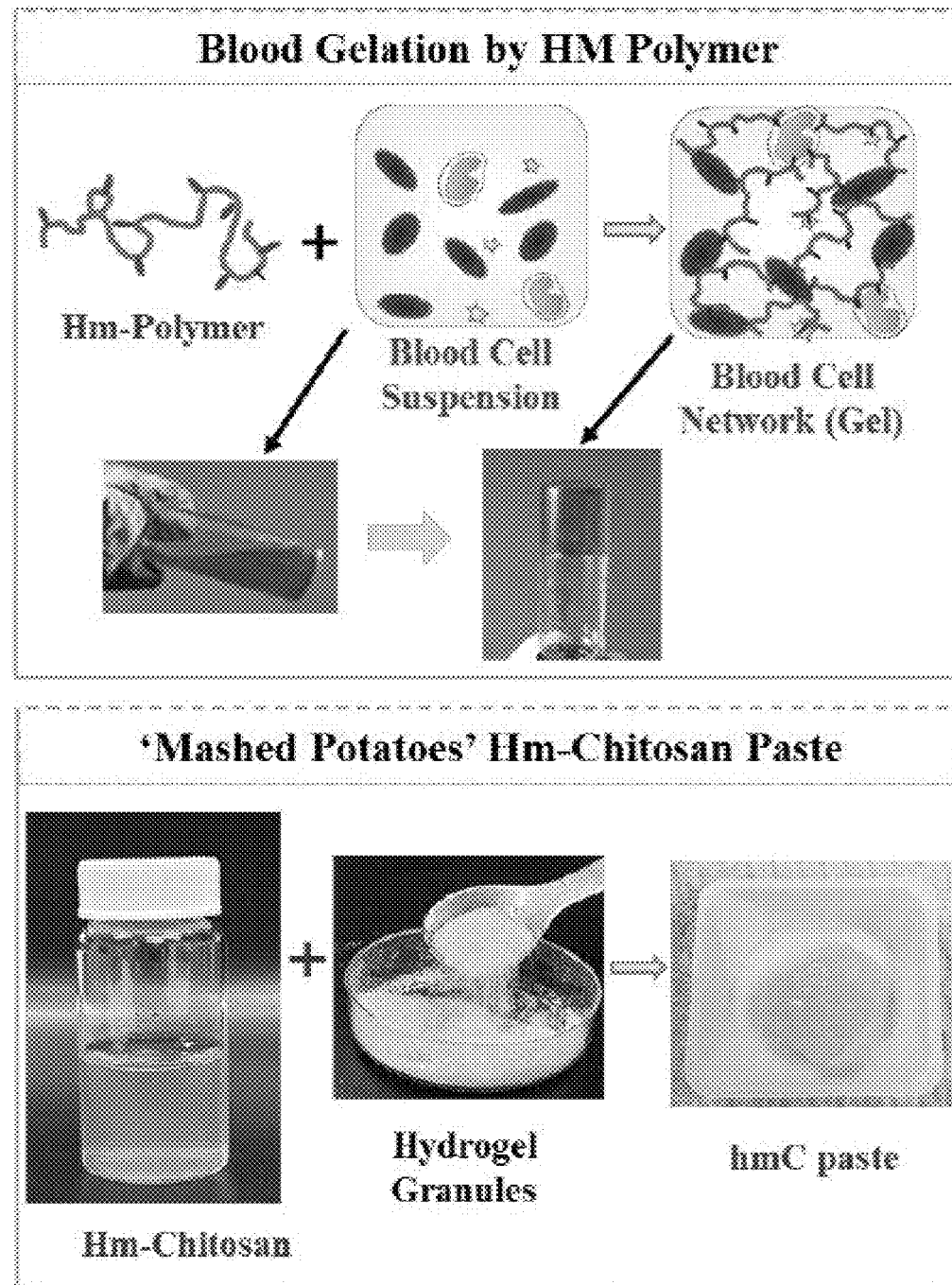
FIG. 6 shows images of blood gelation by an Hm-Polymer (FIG. 6, top), and the paste-like characteristics from adding hydrogel granules (dimethylaminoethyl methacrylate, QDM) into an hm-chitosan solution (referred to as 'mashed potatoes' in FIG. 6, bottom).

Example 4: Addition of Quaternized Dimethylaminoethyl Methacrylate (ODM) Particles into An Hm-Chitosan Solution In the experiments of this example (FIG. 6, top, and FIG. 6, bottom) particles were added into hm-chitosan gels in order to create flow resistance against blood that would enter the polymer matrix upon application to a bleeding site. In these experiments, 0.05 g/ml of quaternized dimethylaminoethyl methacrylate (QDM) particles were added into a hm-chitosan solution and the paste-like characteristics were observed on a weigh boat (FIG. 6A and FIG. 6B). The results of the experiments indicated the observation of a pasty and "mashed-potato-y" quality for the particle containing QDM and hm-chitosan. Thus, the addition of QDM particles in a hm-chitosan solution created a pasty and "mashed-potatoe-y" character of the hm-chitosan, and this particle addition can be used as a tool to modify the material handling characteristics of the gel.

Figure 7:
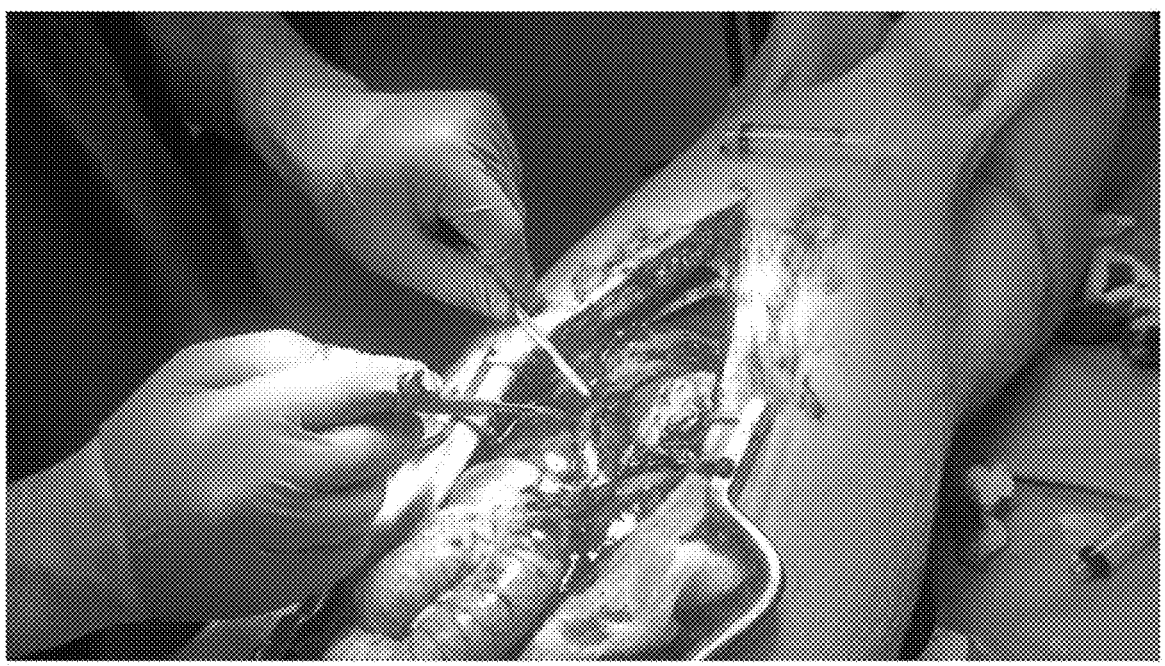
FIG. 7 is an image showing the formulation of QDM particles and Hm-Chitosan gels in an in vivo model of bleeding.

Particles were added into hm-chitosan gels to create flow resistance against blood that would enter the polymer matrix upon application to a bleeding site in vivo. These experiments were performed to assess how well quaternized dimethylaminoethyl methacrylate (QDM) particles and hm-chitosan gels would perform in an in vivo model of bleeding. To carry out these experiments, the "mashed potato" like substance (i.e., QDM particles and hm-chitosan gels) was taken to an animal lab and tested on 15 mm×15 mm liver squares in swine (FIG. 7). After application to the site, compression was applied for 2 minutes. The mashed potato formulation (i.e., QDM particles and hm-chitosan gels) worked well in the bleeding model and was able to be compressed with gauze without being pulled off by the gauze after application. The bleeding score dropped from a 3 to 1 after 2 minutes of compression. Therefore, the mashed potato formulation (i.e., QDM particles and hm-chitosan gels) is useful as a hemostatic material for minor soft tissue bleeding. These studies further suggest that other particles gels, such as dextran particles, would provide similar advantages. Exemplary formulations would include about 0.5% to about 1.0% by weight of dextran particles.

Example 5: Addition of Polyethylene Oxide (PEO) Into Hm-Chitosan Foams

Figure 8:
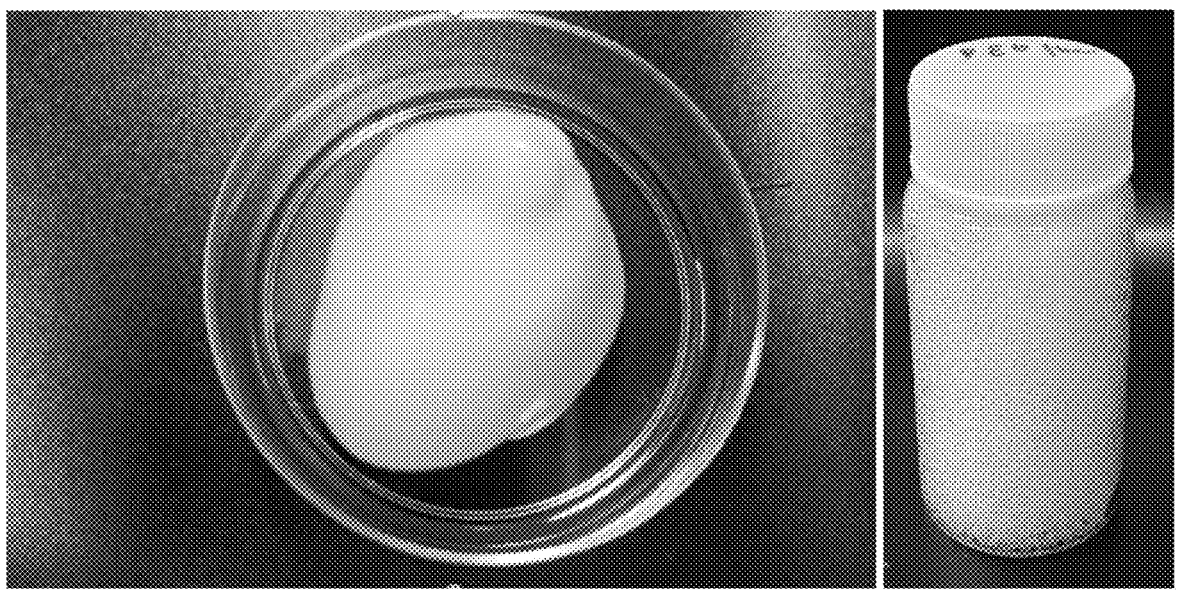
FIG. 8 is an image showing stable hm-chitosan and polyethylene oxide (PEO) foams.
Figure 9:
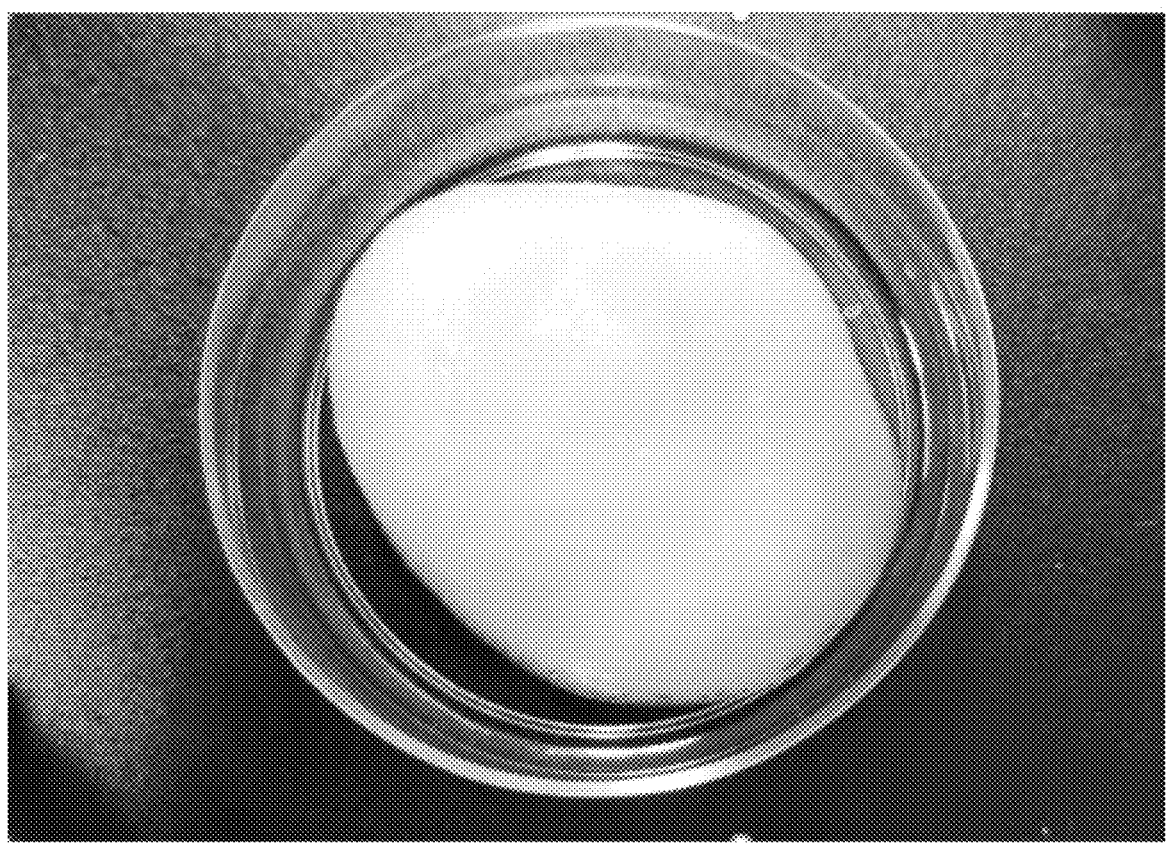
FIG. 9 is an image showing a stable foam with the addition of pluronics (i.e., non-ionic surfactants) in the HM-CS foams.

The experiments of this example show further increased stability of foams by introduction of amphiphilic polymer at the gas/hm-chitosan polymer interface. (see FIG. 8). In a double barrel syringe, one barrel was filled with 2 wt % hm-chitosan and second barrel with 3 wt % polyethylene oxide (PEO), and foams were generated. The experiments demonstrated that the foams were more stable than hm-chitosan foams without the addition of PEO. The hm-chitosan-PEO foams did not get dissipated on tapping with spatula. Thus, the hm-chitosan-PEO foams have good mechanical integration and elasticity, which could be helpful for achieving hemostasis without getting dissipated easily by gauze compression.

Example 6: Addition Of Pluronics In HM-CS Foams

In the experiments of this example, pluronics (i.e., non-ionic surfactants) were added in the hm-chitosan foams. The addition of pluronics in the hm-chitosan foams increased the stability of the foams by introducing an amphiphilic polymer at the gas/hm-chitosan polymer interface. To carry out the experiments, a double barrel syringe was used, where one barrel was filled with 2 wt % hm-chitosan and the second barrel was filled with 5 wt % Pluronic 123, and foams were generated. The experiments demonstrated that the foams generated with pluronics were more stable than hm-chitosan foams without the addition of pluronics. The pluronic-hm-chitosan foams did not get dissipated on tapping with spatula, and retained their structure even after multiple tapping. Therefore, hm-chitosan-pluronics foams have good mechanical integration and elasticity that would be useful for achieving hemostasis without getting dissipated easily by gauze compression.

Example 7: Hydrophobically-Modified Chitosan (hmC) and Hydrophobically-Modified Alginate (hmA) Foams Exhibit Enhanced Rheological and Hemostatic Properties The purpose of the experiments detailed in this example was to show that foams based on mixtures of two hemostatic biopolymers, hmC (cationic) and hmA (anionic), have enhanced rheological properties as compared to foams based on hmC alone. For example, it was shown that the carbon dioxide ($CO_2$) gas bubbles in this foam were stabilized by hmC and hmA chains that collectively form a coacervate (i.e., a distinct phase formed by liquid-liquid phase separation in mixtures of oppositely charged polymers or surfactants) that surrounds the bubbles, and that this coacervate stabilization has significant effects on the properties of the foam.

Synthesis of hmC and hmA

To synthesize hmC, 1 wt % chitosan was first dissolved in 0.2 M acetic acid. An equal volume of ethanol was then added, and the solution was heated to 65° C. Palmitic anhydride was dissolved in a separate beaker with ethanol and heated to 65° C. The anhydride solution was then added to the chitosan solution such that the stoichiometry corresponded to 1.5 mol % of the amines on the chitosan. The mixture was allowed to react overnight, whereupon the hmC was formed. To precipitate the hmC from this solution, the pH was raised by adding NaOH. The precipitate was then washed with ethanol several times and left to dry, then ground into a powder. The resulting hmC had $C_{16}$ hydrophobes with a degree of hydrophobe modification of 1.5%.

To synthesize hmA, 2 wt % alginate was dissolved in water using HCl to make the solution acidic (with a pH of approximately 3.4). An aqueous solution of EDC (0.66 grams of EDC for every gram of alginate) was then added to this solution, followed by the addition of n-octylamine (0.91 grams of octylamine for every gram of alginate) dissolved in 50/50 water/ethanol. The reaction was allowed to run for 24 hours to form the hmA. The hmA was precipitated out by adding acetone into the reaction mixture. This precipitate was then washed several times with acetone and allowed to dry, then ground into a powder. The resulting hmA had $C_8$ hydrophobes with a degree of hydrophobe modification of 25%.

Coacervation

Figure 10A:
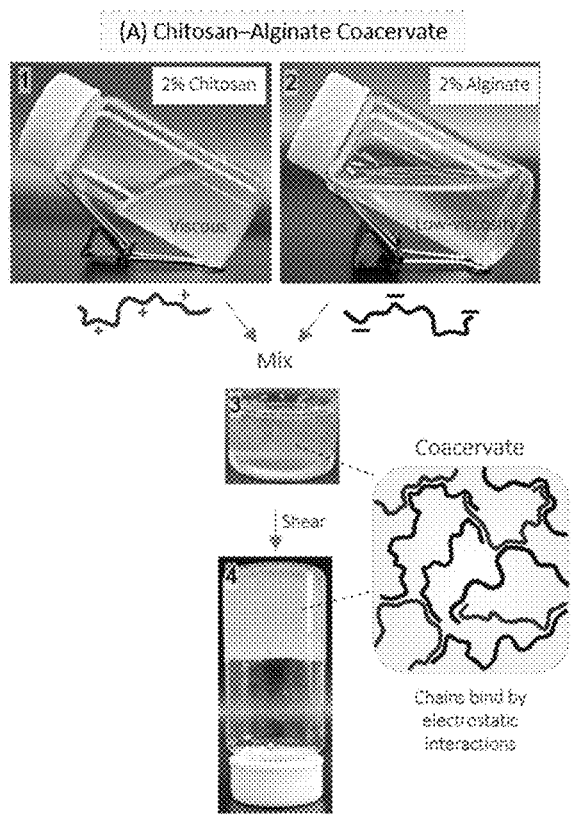
FIGS. 10A-B depict coacervate formation in chitosan-alginate and hmC-hmA mixtures.

The phenomenon of coacervation in chitosan-alginate solutions was shown. FIG. 10A shows vials containing a 2% chitosan solution (in acetic acid) and a 2% alginate solution (in deionized or DI water). Chitosan has a pKa of 6.5 and thus in acidic media, its chains are cationic due to the protonation of amines along their backbone. Alginate chains, on the other hand, are anionic in solution due to the dissociation of their carboxylate groups. The chitosan used here has a high molecular weight and a 2% solution of this chitosan is thereby quite viscous (FIG. 10A, Photo 1). The 2% alginate solution is of a lower viscosity and flows readily in the tilted vial (FIG. 10A, Photo 2). When the two solutions are gently mixed, discrete globs of a gooey material (the coacervate) are instantly formed, and these globs remain suspended in a clear external solution (FIG. 10A, Photo 3). Upon shearing this sample using a vortex mixer, the globs are reduced in size and eventually, the entire sample appears near-homogenous and turbid. The sample shows elastic or gel-like character, as reflected in its ability to hold its weight in the inverted vial (FIG. 10A, Photo 4).

Figure 10B:
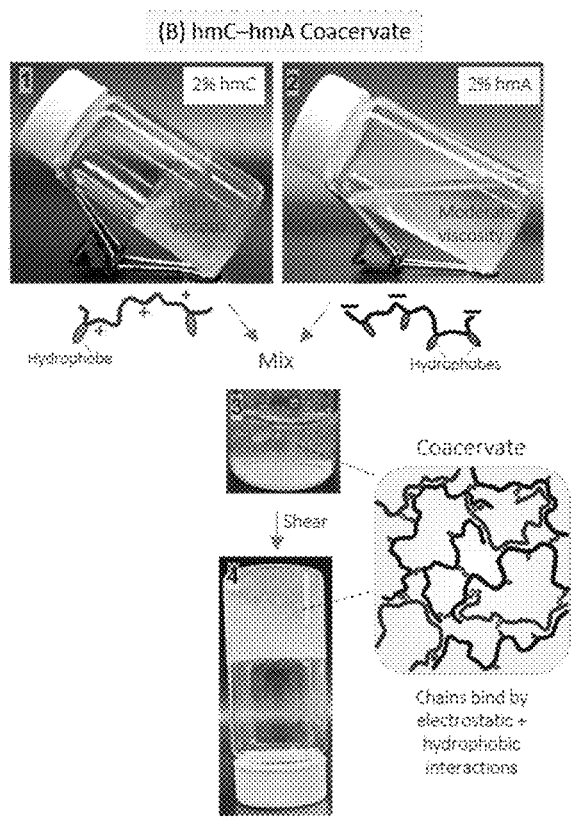

Similar results were observed in hmC-hmA solutions. The hmC has hexadecyl (C16) tails attached to 1.5% of the amines along the chitosan backbone. The hydrophobes allow hmC chains to associate and thereby thicken the solution. This is why a 2% hmC solution is extremely viscous (see, FIG. 10B, Photo 1). In the case of the hmA, it has octyl (C8) tails attached to 25% of the carboxylates along the alginate backbone. Because the hydrophobes are shorter, the 2% hmA solution is only moderately viscous (FIG. 10B, Photo 2). When the hmC and hmA solutions are mixed, the result is similar to that for chitosan-alginate: discrete globs of the coacervate appear (FIG. 10B, Photo 3), and upon shearing, the globs are homogenized into a gel-like sample (FIG. 10B, Photo 4). This coacervate gel is expected to contain a network of the hmC and hmA chains bound via both electrostatic and hydrophobic interactions.

Foam Generation

Figure 11A:
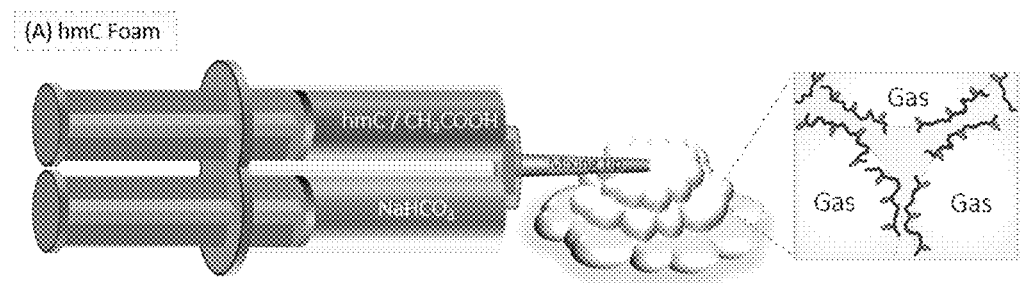
FIGS. 11A-B depict foam generation using a double-barrelled syringe (DBS).
Figure 11B:
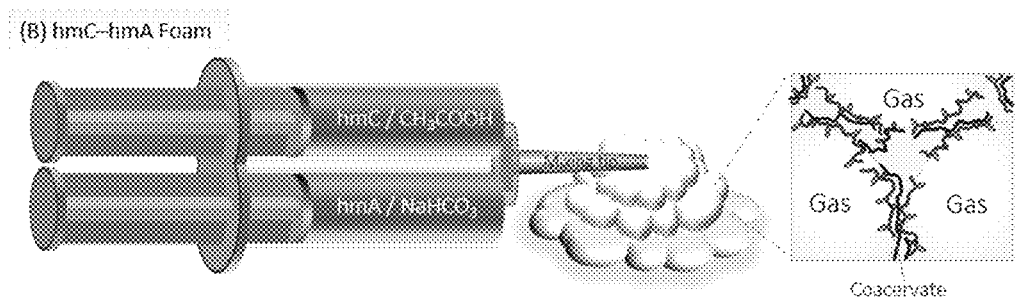

To generate the foams in the study, a double-barrelled syringe (DBS) was used, as schematized in FIG. 11. The foam was formed via the reaction of an acidic solution (acetic acid, $CH_3COOH$) and a basic solution (sodium bicarbonate, $NaHCO_3$) loaded in separate barrels of the DBS. The two solutions come into contact at the mixing tip, whereupon the following reaction occurs:

$$CH_3COOH + NaHCO_3 \rightarrow CH_3COONa + CO_2 (g) + H_2O \qquad (1)$$

The net result is the formation of carbon dioxide ($CO_2$) gas in the form of bubbles. The experiment investigates surfactant-free foams due to their intended use in biomedical applications. Therefore, an amphiphilic polymer (hmC or hmA or both) must be included for foam formation.

The key contrast in this experiment is between a foam made with hmC or hmA alone and one with both hmC and hmA. In the case of the hmC foam (FIG. 11A), one barrel of the DBS had a solution of hmC in 1.1 M $CH_3COOH$ and the other had a solution of 1.1 M $NaHCO_3$. The bubbles in this foam were stabilized by hmC chains and no coacervate. In the case of the hmC-hmA foam (FIG. 11B), the first barrel had the hmC solution as before, while the other barrel had a solution of hmA in the base. The bubbles in this foam were stabilized by hmC and hmA chains collectively in a coacervate (or, put differently, the coacervate surrounded the bubbles).

Foam Appearance, Stability, and Microstructure

First, visual observations and optical microscopy were used to contrast an hmC-hmA foam and one with hmC. The foams with hmC or hmA alone are similar in most respects, and so the contrast is made with the hmC one.

FIG. 12A shows photos of a foam made with 4% hmC and FIG. 12B shows photos of a foam made with 2% hmC and 2% hmA. The concentrations were chosen such that the total polymer content in the two foams was the same. Both these foams expand when released out of the DBS tip, but they have different textures. Foam stability was studied by injecting the above foams into vials and measuring the height of the foams as time progressed. The hmC foam reduced appreciably in height within 30 min, with some of the dissipated foam remaining stuck to the vial walls. The hmC-hmA foam, on the other hand, remained stable for a much longer time and reduced to about half its height in about hours. Thus, hmC-hmA mixtures impart greater stability to the foam compared to hmC alone.

Next, the mechanical (rheological) properties of the foams in their stable, expanded state were studied. The different rheology exhibited by the foams is reflected in the photos in FIG. 12A-B. Test 1 shown in FIGS. 12A and 12B compared the responses of the foams to a gentle perturbance from a spatula. When an area of the hmC foam was tapped by the spatula, the bubbles dissipated and the foam collapsed over the disturbed area. This shows the fragility of the hmC foam. In contrast, when the hmC-hmA foam was tapped by the spatula, the foam deformed over the affected area, but it did not dissipate or collapse. Instead, the hmC-hmA foam exhibited an elastic response—i.e., it recoiled against the applied deformation. Test 2 shows the differences between the foams in another way. Here, each foam was placed between parallel plates and the top plate was brought down to compress the foam. After compression to half its initial height for a minute, the top plate was retracted to its initial height. FIG. 12A reveals that the compression caused much of the bubbles in the hmC foam to dissipate. When the plate was raised back, the residue from the foam adhered to each plate but most of the bubbles in the middle had disappeared. This demonstrates the inability of the hmC foam to withstand compressive stress. Conversely, the bubbles did not break in the hmC-hmA foam when the plates were compressed (FIG. 12B). When the plate were raised back, the foam stuck to both plates but still retained its integrity. In summary, the differences between the above foams can be described as analogies to common foams: the texture or consistency of the hmC foam was similar to that of a frothy material such as a shower foam, whereas the hmC-hmA foam had a consistency comparable to that of a thick mousse or meringue.

Figure 13A:
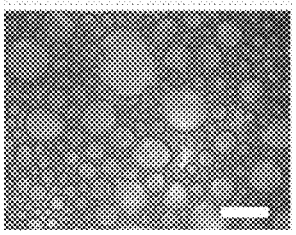
FIGS. 13A-D exhibit optical micrographs of foams with various polymer content: 2% hmC (FIG. 13A); 4% hmC (FIG. 13B); 1% hmC+1% hmA (FIG. 13C); 2% hmC+2% hmA (FIG. 13D), and their corresponding bubble size distributions.
Figure 13A:
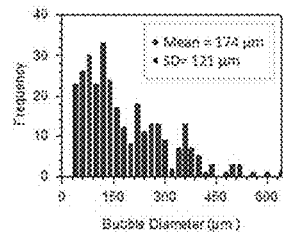
Figure 13B:
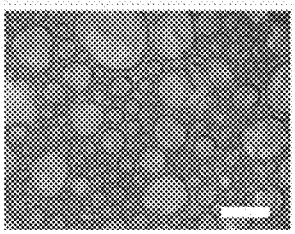
Figure 13B:
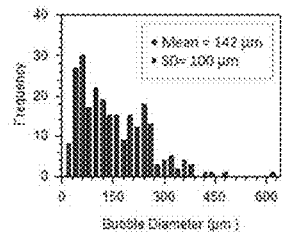
Figure 13C:
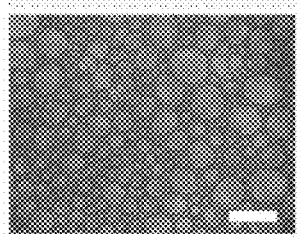
Figure 13C:
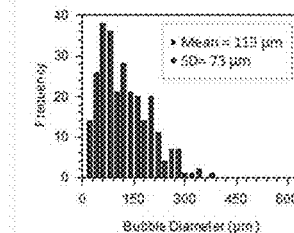
Figure 13D:
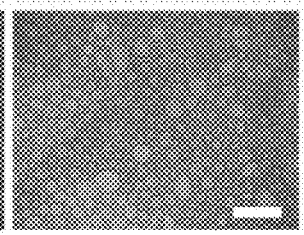
Figure 13D:
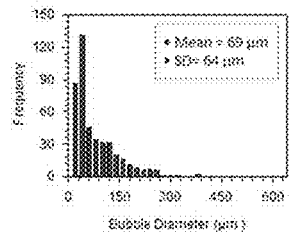

Then, the hmC and hmC-hmA foams were characterized by optical microscopy. Representative images are provided for hmC foams (FIGS. 13A-B) and hmC-hmA foams (FIGS. 13C-D) at total polymer concentrations of 2% and 4%. In all cases, as expected, the images show numerous bubbles that fill up the entire view. The bubbles were not close-packed in the hmC foams (bubble volume fraction 50-60%) and small gaps were seen between the bubbles. By contrast, the bubbles appear nearly close-packed in the hmC-hmA foams (bubble volume fraction 60-70%), although Plateau borders are not seen between the bubbles (which would arise if the bubbles were tightly packed). Bubble sizes from these images were analysed using ImageJ and the distributions are provided for each sample. A striking observation is that the bubbles were much smaller in the hmC-hmA foams than in the hmC foams. The mean diameter of the bubbles was calculated from each distribution. This diameter is 174 and 142 μm for the 2% and 4% hmC foams, whereas it is 113 and 69 μm for the 2% and 4% hmC-hmA foams. Additionally, there are very few bubbles larger than 200 μm in the hmC-hmA foams whereas the hmC foams have many such bubbles. It is also noted from the y-axes that there are far more bubbles in the hmC-hmA foams compared to the hmC ones.

Foam Rheology

Figure 14A:
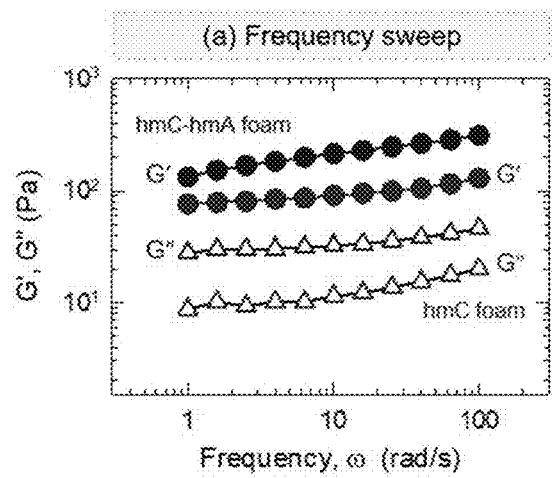
FIGS. 14A-D show dynamic rheology of hmC and hmC-hmA foams.
Figure 14B:
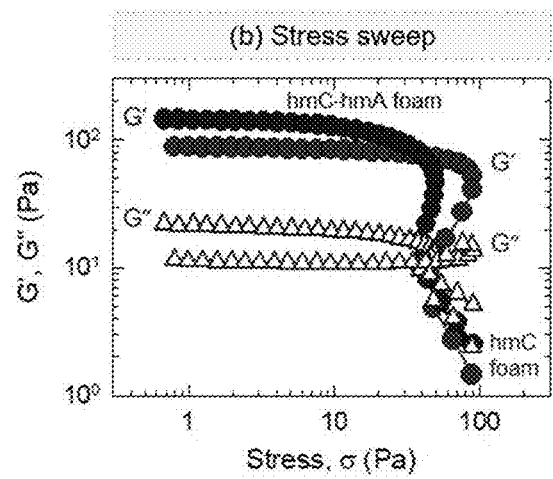

The rheological properties of hmC and hmC-hmA foams were then measured. First, foams with 4% hmC and 2% hmC+2% hmA were compared using dynamic rheology (oscillatory shear). FIG. 14A shows a plot of G' and G" as functions of @. Both foams showed an elastic response, with G'>G" and the moduli were nearly independent of frequency. The response indicated the solid-like behaviour of the foams at low deformations (within the linear viscoelastic regime of the samples). The key parameter from the plots is the elastic modulus G', which was about 250 Pa for the hmC-hmA foam and 100 Pa for the hmC foam. Next, the frequency was kept constant at 10 rad/s and G' and G" were measured against the stress-amplitude σ for both foams. FIG. 14B shows that the moduli were independent of σ at low stresses and then, beyond a critical stress (i.e., the yield stress σy), the moduli rapidly decreased. From these plots, σy is about 50 Pa for both foams, i.e., there were no significant differences in this parameter between the two.

Figure 14C:
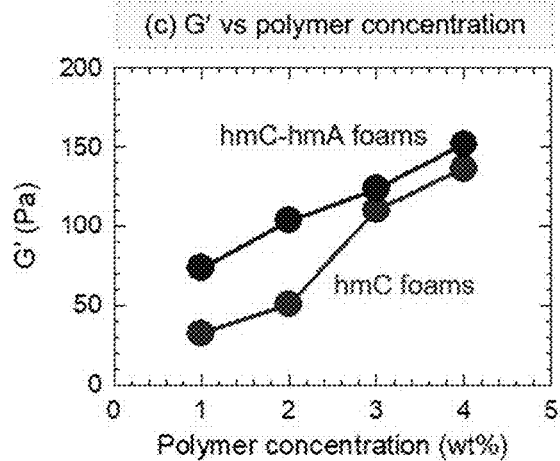

Additionally, the variation of the foam modulus G' with polymer concentration was examined for both the hmC and the hmC-hmA foams. The latter had equal concentrations of the two polymers—e.g., a 2% foam corresponded to 1% hmC+1% hmA. Dynamic rheology was performed on each sample and data for G' at a frequency of 10 rad/s are plotted in FIG. 14C. The results indicate that the hmC-hmA foams have higher G' values (G' is a measure of the stiffness of the foam) across the concentration range.

Figure 14D:
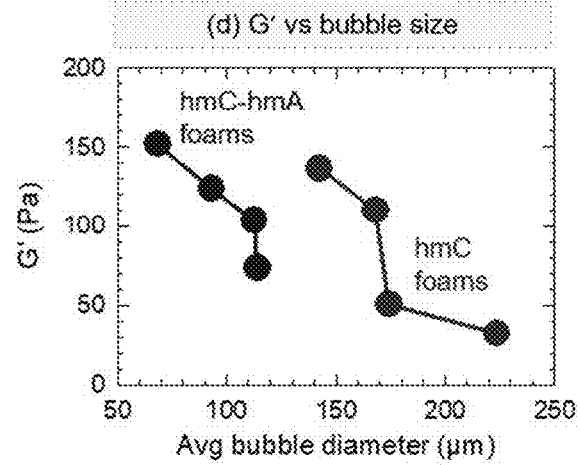

FIG. 14D shows plots of G' against the average bubble diameter obtained from optical microscopy. This relationship is shown for both the hmC and the hmC-hmA foams. In both cases, G' does increase as the bubbles get smaller. However, the two sets of foams do not overlap on this plot, indicating that the nature of the stabilizer (a single polymer vs. a coacervate) does influence the foam rheology. The bubble diameters were considerably smaller across the entire concentration range for the hmC-hmA foams as compared to the hmC foams.

Studies with Blood

Figure 15A:
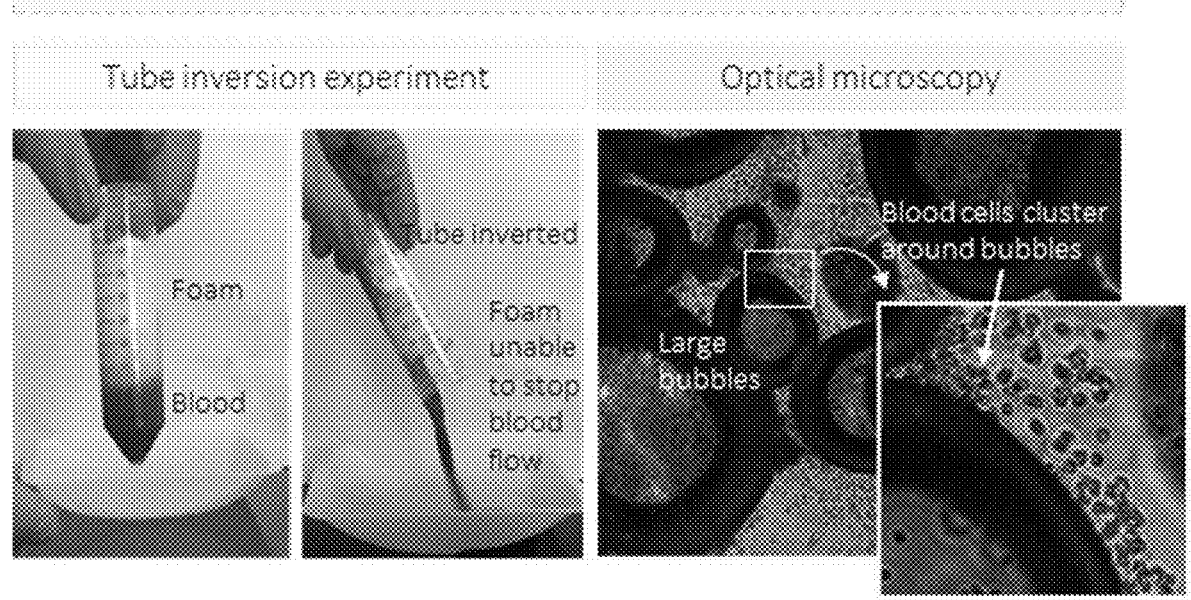
FIGS. 15A-B depict a tube inversion test to examine foam-blood interactions, where
Figure 15B:
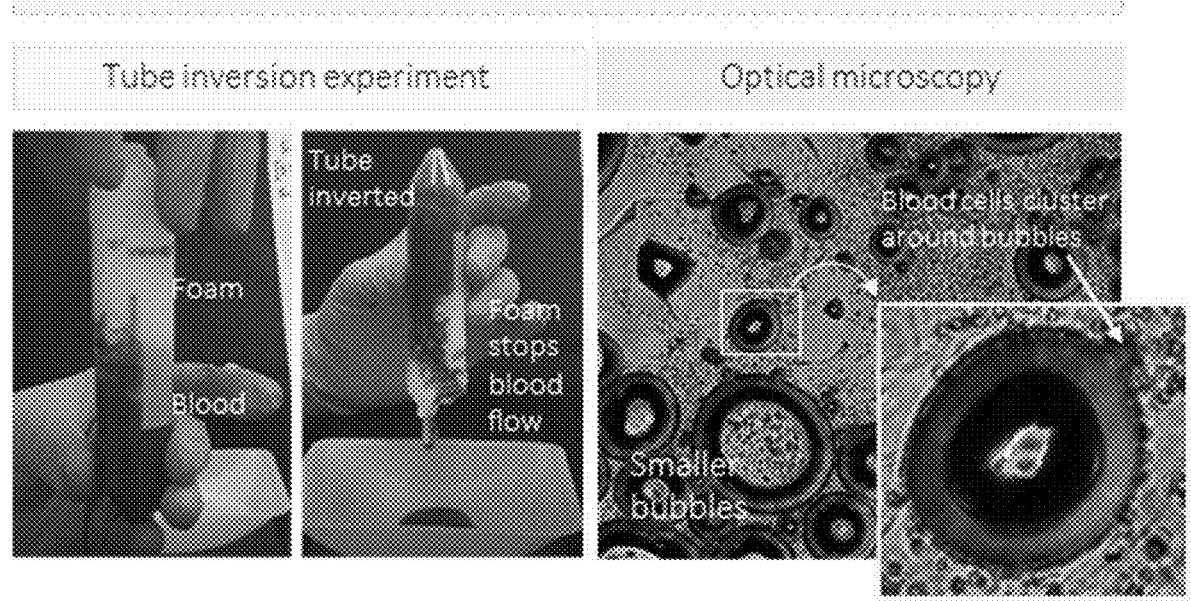

The use of hmC-hmA foams as hemostatic materials, i.e., to stop bleeding were examined. To examine this ability, experiments were conducted in vitro with the foams in conjunction with blood. A simple tube-inversion test served as a preliminary indicator in this regard. In brief, 10 mL of heparinized bovine blood was first added to a 50 mL centrifuge tube. The foam (volume of 2 mL in each barrel of the DBS=4 mL total) was injected into the tube from the nozzle of the DBS. The foam then expanded and filled the headspace in the tube. The tube was then inverted to see whether the foam could hold back the blood (FIGS. 15A-B). In the case of the 4% hmC foam, the blood immediately flowed through the foam upon tube inversion (FIG. 15A), indicating that this foam did not constitute a sufficient mechanical barrier to blood flow. In contrast, the foam of 2% hmC+2% hmA was able to hold back the blood in the inverted tube for several minutes, confirming its greater mechanical integrity. Increasing the polymer concentration to 4% hmC+4% hmA was enough to hold back 10 mL of blood for over 20 minutes. The amount of blood was then doubled to 20 mL and the test was repeated with this foam. The foam was able to hold back the blood flow for over 15 minutes (FIG. 15B). These results show that hmC-hmA foams are advantageous for hemostatic purposes.

To probe the interactions between the foams and blood, optical microscopy was also used. For these experiments, heparinized blood was diluted 10× in saline to ensure visibility of blood cells. The foams were mixed with this blood and then studied under bright-field microscopy. The images in FIG. 15A (for an hmC foam) and in FIG. 15B (for an hmC-hmA foam) both show blood cells clustering around the gas bubbles. Thus, the hm-polymers do behave as active hemostatic agents. But for the polymers to interact with blood, sufficient contact time is needed. If the foam fails to provide a mechanical barrier, this contact time will be insufficient—and this was the case for the hmC foam (FIG. 15A). In these in vitro experiments, clotting of blood via the usual clotting cascade has been eliminated by addition of heparin. In the case of in vivo experiments (see below), both the hm-polymers and the clotting cascade will act synergistically to immobilize the blood.

Hemostatic Studies

Figure 16A:
FIGS. 16A-B depict a comparison of an hmC (FIG. 16A) and an hmC-hmA foam (FIG. 16B) as hemostatic agents over actively bleeding wounds in pigs.
Figure 16A:
Figure 16A:
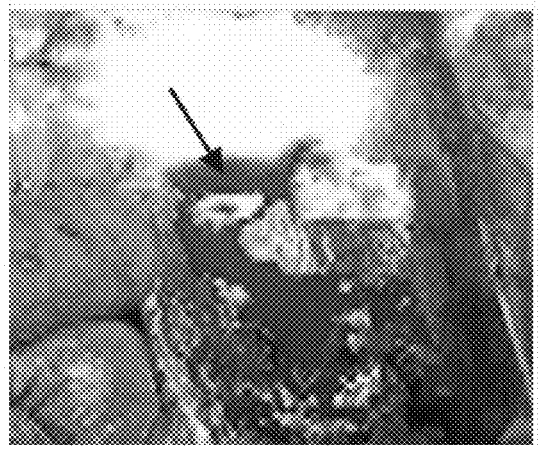
Figure 16B:
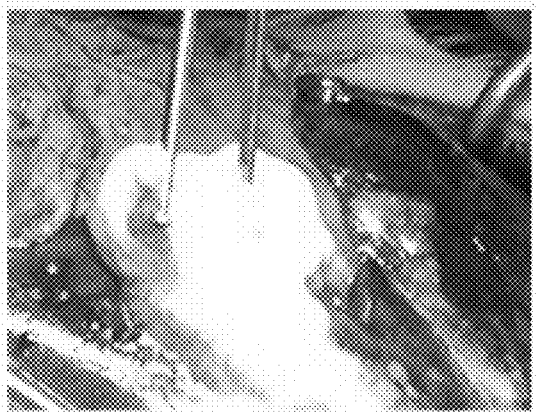
Figure 16B:
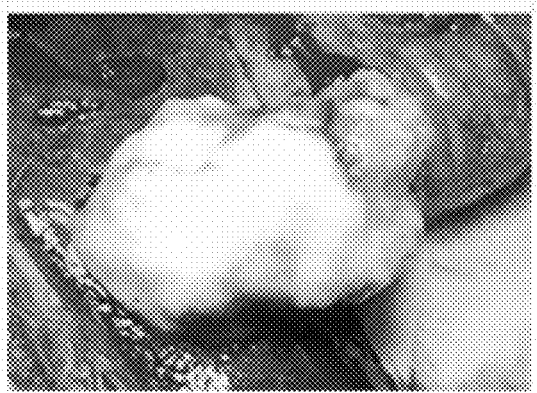
Figure 16B:

The hemostatic efficacy of hmC-hmA foams was tested in pig liver-injury models. Initially a 2% hmC foam (out of a canister) and a 4% hmC+4% hmA foam (out of a DBS) were compared over an actively bleeding pig injury (FIGS. 16A-B). Identical injuries were made using a 10 mm dermal punch and scissors, cutting a hole with a 10 mm diameter and a depth of several mm into the liver, and thereafter the foams were applied. It was found that the hmC foam held back the blood initially, but after a few minutes, the blood seeped through, meaning that the foam was no longer effective at stopping the bleed. In comparison, the hmC-hmA foam did not allow the blood to trickle through over the same time frame, and so the barrier due to the foam remained intact. The results in FIGS. 16A-B confirm that the hmC-hmA foam established a more robust barrier to blood discharge due to its improved rheological properties. As noted above, once the foam impedes blood, it allows the blood to form a clot (gel) at the wound site, due both to interaction with hmC/hmA from the foam as well as the pig's own clotting cascade.

Figure 17:
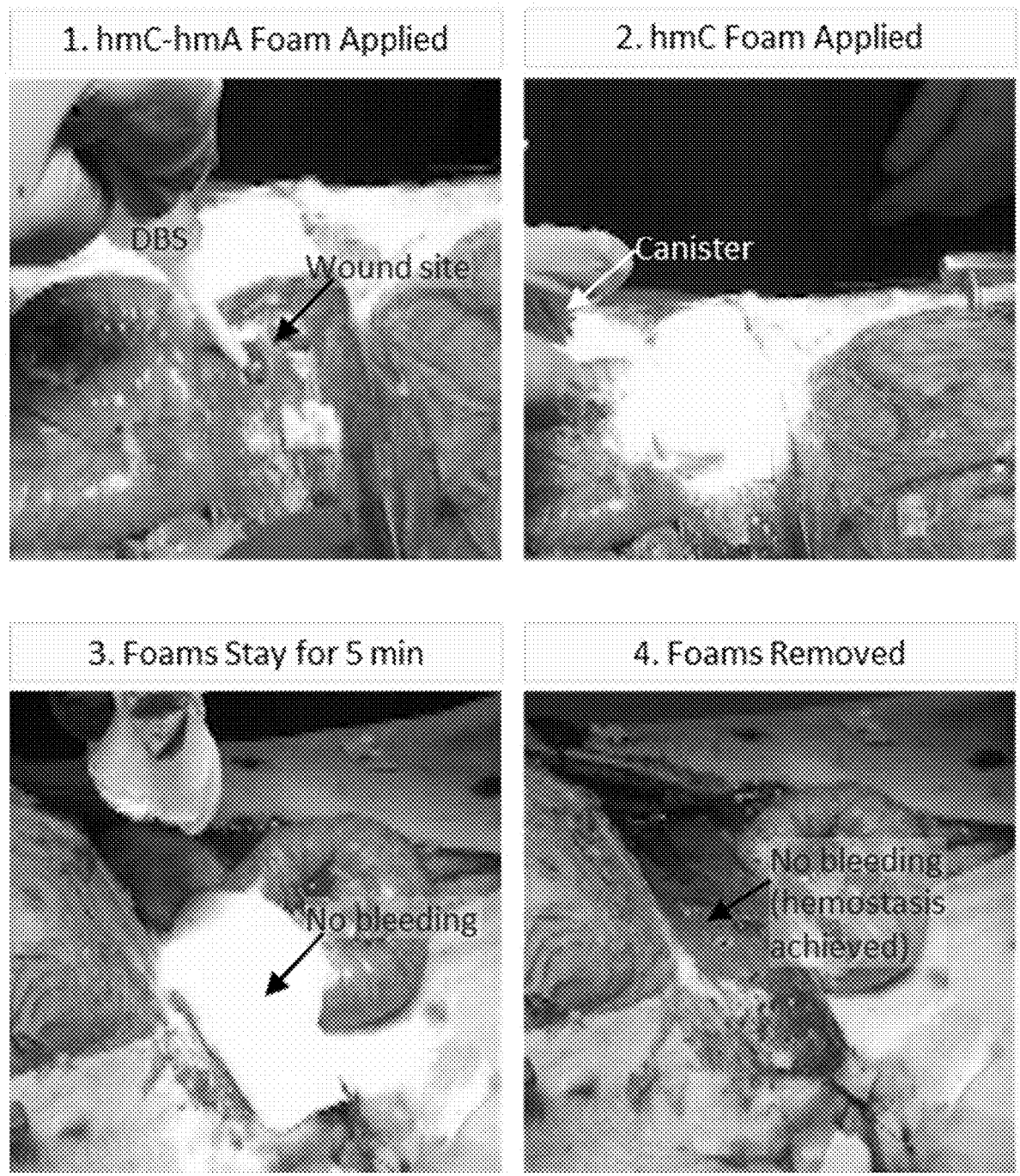
FIG. 17 shows the utilization of both an hmC only foam and an hmC-hmA foam on an actively bleeding pig liver injury.

A test with both foams was conducted and the results are depicted in FIG. 17. A liver injury was made as above with a 10 mm dermal punch. The hmC-hmA foam was first applied, quickly followed by the hmC foam. This combination allowed the hmC-hmA foam to serve as a robust barrier to the bulk of the blood flow while the canister foam completely covered the wound and surrounding area. The foams were allowed to sit for over 5 minutes, during which time no bleeding through the foams was observed. Then, the foams were removed, and even afterwards, no additional bleeding occurred, indicating that hemostasis had been achieved. These results indicate that the combination of the two foams (hmC-hmA from the DBS and hmC alone from the canister) could be a viable strategy to address large internal wounds.

REFERENCES

1. De Castro, G. P., Dowling, M. B., Kilbourne, M, Keledjian, K., Driscoll, I. R., Raghavan, S. R., Hess, J. R., Scalea, T. M., Bochicchio, G. V., "Determination of efficacy of a novel modified chitosan sponge dressing in a lethal arterial injury model in swine" *J. Trauma*, 72 (4), 899-907 (2012).
2. M. B. Dowling, R. Kumar, M. R. Keibler, J. R. Hess, G. V. Bochicchio, S. R. Raghavan, "A self-assembling hydrophobically-modified chitosan capable of reversible hemostatic action" Biomaterials. 32, (13) 3351-3357 (2011).
3. J. H. Lee, J. P. Gustin, T. Chen, G. F. Payne and S. R. Raghavan, "Vesicle-biopolymer gels: Networks of surfactant vesicles connected by associating biopolymers." Langmuir 21, 26 (2005).
4. Wu, P., Luchessi, L., Guo, J., Prahl, S., Gregory, K. "Development of in vitro adhesion test for chitosan bandages" (open web publication).

What is claimed is:

1. A hemostatic product comprising a container having at least two compartments each containing a releasable, flowable product: wherein a first compartment comprises a solution having a concentration from about 0.1 wt % to about 5 wt % of an acidified hydrophobically-modified chitosan that creates hemostasis and has a pH of from about 2 to about 4.5, and a second compartment comprises a solution of a bicarbonate or carbonate salt at an alkaline pH, wherein the hydrophobic modifications of the chitosan comprise linear hydrocarbon groups in the range of C6 to C18.

2. The product of claim 1, wherein the linear hydrocarbon groups are independently selected from C12, C14, and C16 hydrocarbon chains.

3. The product of claim 1, comprising:
(a) grafts of C6 to C8 in length;
(b) grafts of C10 to C14 in length; and
(c) grafts of C16 to C18 in length.

4. The product of claim 3, wherein the hydrocarbon groups comprise or consist essentially of C8, C12, and C16 hydrocarbon groups.

5. The product of claim 1, wherein the hydrophobically-modified polymer has a grafting density from about 1% to about 50% of available functional groups on the polymer backbone.

6. The product of claim 5, wherein the hydrocarbon groups have a grafting density of: about 3% to about 7% C8, about 1% to about 5% C12, and/or about 0.5% to about 3% C16, with respect to available amines.

7. The product of claim 1, wherein one or more compartments comprise one or more foam stabilizing additives.

8. The product of claim 7, wherein the foam stabilizing additives comprise a non-ionic surfactant.

9. The product of claim 1, wherein the hydrophobically-modified polymer solution in the first compartment comprises an organic acid, wherein the organic acid is selected from acetic acid, lactic acid, ascorbic acid, and citric acid.

10. The product of claim 9, wherein the hydrophobically-modified polymer solution in the first compartment comprises from about 0.5 to about 2M acetic acid in water.

11. The product of claim 1, comprising a sodium bicarbonate solution in the second container.

12. A method for treating a wound in a body cavity of a mammal, comprising: releasing contents of the product of claim 1 into a cavity comprising the wound.

13. The method of claim 12, wherein the wound is a non-compressible hemorrhage.

14. A hemostatic product comprising a container having at least two compartments each containing a releasable, flowable product: wherein a first compartment comprises a solution having a concentration from about 0.1 wt % to about 5 wt % of an acidified cationic hydrophobically-modified chitosan that creates hemostasis and has a pH of from about 2 to about 4.5, and a second compartment comprises a solution of a bicarbonate or carbonate salt at an alkaline pH and an anionic polymer, wherein the hydrophobic modifications of the chitosan comprise linear hydrocarbon groups in the range of C6 to C18.

15. A method of treating a bleeding wound, comprising: releasing contents of the product of claim 14 to the bleeding wound.

\* \* \* \* \*